US009119401B2

(12) United States Patent
Huang et al.

(10) Patent No.: US 9,119,401 B2
(45) Date of Patent: Sep. 1, 2015

(54) PLANT GLUTAMINE SYNTHETASE INHIBITORS AND METHODS FOR THEIR IDENTIFICATION

(71) Applicant: Marrone Bio Innovations, Inc., Davis, CA (US)

(72) Inventors: Huazhang Huang, Woodland, CA (US); Ratnakar Asolkar, Davis, CA (US); Pamela Marrone, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 144 days.

(21) Appl. No.: 13/841,963

(22) Filed: Mar. 15, 2013

(65) Prior Publication Data

US 2014/0113816 A1    Apr. 24, 2014

Related U.S. Application Data

(60) Provisional application No. 61/716,467, filed on Oct. 19, 2012.

(51) Int. Cl.
*C12Q 1/00* (2006.01)
*A01N 63/00* (2006.01)

(52) U.S. Cl.
CPC ..................................... *A01N 63/00* (2013.01)

(58) Field of Classification Search
None
See application file for complete search history.

(56) References Cited

U.S. PATENT DOCUMENTS

| | | | |
|---|---|---|---|
| 4,808,207 A | 2/1989 | Gottlieb | |
| 5,545,542 A | 8/1996 | Nakajima | |
| 5,902,595 A | 5/1999 | Burklow | |
| 5,948,612 A * | 9/1999 | Bascomb et al. | 435/6.15 |
| 6,077,505 A | 6/2000 | Parke | |
| 6,194,194 B1 | 2/2001 | Molloy | |
| 6,384,186 B2 | 5/2002 | Anke | |
| 6,689,357 B2 | 2/2004 | Casida | |
| 7,141,407 B2 | 11/2006 | Zhang | |
| 7,393,812 B2 | 7/2008 | Gerwick | |
| 7,396,665 B2 | 7/2008 | Ueda | |
| 7,923,005 B2 | 4/2011 | Rao | |
| 8,822,193 B2 | 9/2014 | Asolkar | |
| 2003/0082147 A1 | 5/2003 | Gouge | |
| 2004/0071663 A1 | 4/2004 | Campos | |
| 2007/0191228 A1 * | 8/2007 | Li et al. | 504/117 |
| 2008/0096879 A1 | 4/2008 | Koide | |
| 2009/0175837 A1 | 7/2009 | Yuki | |
| 2010/0022584 A1 | 1/2010 | Kenyon | |
| 2011/0207604 A1 | 8/2011 | Asolkar | |
| 2014/0056853 A1 | 2/2014 | Marrone | |

FOREIGN PATENT DOCUMENTS

| | | |
|---|---|---|
| JP | 2007-091701 | 4/2007 |
| KR | 2005-003400 A | 4/2005 |
| KR | 100537389 B1 | 12/2005 |
| WO | WO 97/20857 | 6/1997 |
| WO | 01/55398 | 8/2001 |
| WO | WO 01/55143 | 8/2001 |
| WO | WO 2009/049378 | 4/2009 |
| WO | WO 2013/032693 | 3/2013 |

OTHER PUBLICATIONS

Sinden et al., Nature, vol. 219, Jul. 27, 1968, pp. 379-380.*
Omura et al., The Journal of Antibiotics, vol. 37, No. 8, 1984, pp. 829-835.*
Duke, Environmental Health Perspectives, vol. 87, pp. 263-271, 1990.*
U.S. Appl. No. 14/336,601, Asolkar.
Abdel-Mawgoud et al., "Rhamnolipids: Diversity of Structures, Microbial Origins and Roles", Applied Microbiology and Biotechnology 86: 1323-1336. 2010.
Anderson et al., "The Structure of Thiostrepton" Nature 225: 233-235. 1970.
Andra, "Endotoxin-Like Properties of a Rhamnolipid Exotoxin from Burkholderia (Pseudomonas) Plantarii: Immune Cell Stimulation and Biophysical Characterization" Biol. Chem. 387: 301-310. 2006.
Arena et al., "The Mechanism of Action of Avermectins in *Caenorhabditis elegans*—Correlation Between Activation of Glutamate-Sensitive Chloride Current, Membrane Binding and Biological Activity" J. Parasitol. 81: 286-294. 1995.
Asolkar et al., "Daryamides A-C Weakly Cytotoxic Polyketides from a Marine-Derived Actinomycete of the Genus *Streptomyces* Strain CNQ-085" J. Nat. Prod. 69:1756-1759. 2006.
Battu et al., "Development and Validation of RP-HPLC for the Rabeprazole Sodium in Pharmaceutical Formulations and Human Plasma", Asian J. Research Chem. 2(1 ): 49-51 Jan.-Mar. 2009.
Betti et al., "Molecular Analysis of Two Mutants from Lotus Japonicus Deficient in Plastidic Glutamine Synthetase: Functional Properties of Purified GLN2 Enzymes", Planta 224: 1068-1079. 2006.
Blodget et al., "Molecular Cloning, Sequence Analysis and Heterologous Expression of Phosphinothricin Tripeptide Biosynthetic Gene Cluster from Streptomyces viridochromogenes DSM 40736," Antimicrobial Agents and Chemotherapy 49: 230-240. 2005.
Blodget et al., "Biosynthesis of 2-Hydroxyethylphosphonate, an Unexpected Intermediate Common to Multiple Phosphonate Biosynthetic Pathways," J. Biol. Chem. 22:23161-23168. 2008.
Burkhead et al., "Pyrrolnitrin Production by Biological Control Agent Pseudomonas Cepacia B37w in Culture and in Colonized Wounds of Potatoes", Appl. Environ. Microbiol. 60: 2031-2039. 1994.

(Continued)

*Primary Examiner* — Chris R Tate
*Assistant Examiner* — Douglas F White
(74) *Attorney, Agent, or Firm* — Ying-Horng Liu

(57) ABSTRACT

Provided are methods for identification of plant glutamine synthetase inhibitors as well as the plant synthetase inhibitors identified. Further provided are methods of modulating glutamine synthetase activity in a plant, particularly weeds by applying to the plant or substrate for cultivating the plant a microorganism (e.g. *Burkholderia* strain) in an amount effective to modulate glutamine synthetase activity.

4 Claims, 3 Drawing Sheets

(56) References Cited

OTHER PUBLICATIONS

Burkholder, "Sour Skin, a Bacterial Rot of Onion Bulbs" Phytopathology 40: 115-117. 1950.
Burkholderia andropogonis: Psuedomonas woodsii ,CW00B006C (ATCC PTA-4234) accessed from http://www.atcc.org/Products/All/PTA-4234 on Mar. 12, 2014.
Battu et al., "Development and Validation of RP-HPLC for the Rabeprazole Sodium in Pharmaceutical Formulations and Human Plasma", Asian J. Research Chem. 2(1): 49-51 Jan.-Mar. 2009.
Cordova-Kreylos et al., "Isolation and Characterization of *Burkholderia rinojensis* sp. nov., a Non-Burkholderia cepacia Complex Soil Bacterium with Insecticidal and Miticidal Activities," App. Env. Micro. 79(24):1-10 (2013).
Caballero-Mellado et al., "*Burkholderia unamae* sp. nov., an N2-fixing Rhizospheric and Endophytic Species" Int. J. Syst. Evol. Microbiol. 54: 1165-1172. 2004.
Cain et al., "Synergistic Antimicrobial Activity of Metabolites Produced by a Nonobligate Bacterial Predator," Antimicrobial Agents and Chemotherapy 47: 2113-2117. 2003.
Cashion et al., "A Rapid Method for the Base Ratio Determination of Bacterial DNA" Anal. Biochem. 81: 461-466. 1977.
Castro-Rodriguez et al., "The Glutamine Synthetase Gene Family in Populus", BMC Plant Biology 11:119. 2011.
Chen et al., "*Burkholderia nodosa* Sp. Nov., Isolated from Root Nodules of the Woody Brazilian Legumes Mimosa bimucronata and Mimosa scabrella" Int. J. Syst. Evol. Microbiol. 57: 1055-1059. 2007.
Cheng et al., "Melioidosis: Epidemiology, Pathophysiology, and Management" Clin. Microbiol. Rev. 18: 383-416. 2005.
Coenye et al., "Diversity and Significance of *Burkholderia* Species Occupying Diverse Ecological Niches" Environ. Microbiol. 5: 719-729. 2003.
Compant et al., "Diversity and Occurence of *Burkholderia* spp. in the Natural Environment" FEMS Microbiol. Rev. 32: 607-626. 2008.
De Ley et al., "The Quantitative Measurement of DNA Hybridization from Renaturation Rates" Eur. J. Biochem. 12: 133-142. 1970.
Deng et al., "Structural and Functional Characterization of Diffusible Signal Factor Family Quorum-Sensing Signals Produced by Members of the Burkholderia cepacia complex", Applied and Environmental Microbiology 76: 4675-4683. 2010.
Duke et al., "Natural Products as Sources for Herbicides: Current Status and Future Trends" Weed Res. 40: 99-111. 2000.
El-Banna et al., "Pyrrolnitrin from Burkholderia cepacia: Antibiotic Activity Against Fungi and Novel Activities Against Streptomycetes", J. Applied Microbiology 85: 69-78. 1998.
Eisenberg et al., "Structure—Function Relationships of Glutamine Synthetases", BBA 1477:122-135. 2000.
Gawronski et al., "Microtiter Assay for Glutamine Synthetase Biosynthetic Activity Using Inorganic Phosphate Detection", Analytical Biochemistry 327: 114-118. 2004.
Gising et al., "Trisubstituted Imidazoles as Mycobacterium Tuberculosis Glutamine Synthetase Inhibitors", J. Medicinal Chemistry 55: 2894-2898. 2012.
Grgurina et al., "Novel Cyclic Lipodepsipeptide from *Pseudomonas syringae* pv. lachrymans Strain 508 and Syringopeptin Antimicrobial Activities", Antimicrobial Agents and Chemotherapy, 49:5037-5045. 2005.
Guella et al., "Almazole C, a New Indole Alkaloid Bearing an Unusually 2,5-disubstituted Oxazole Moiety and its Putative Biogenetic Precursors, from a Senegalese Delesseriacean Seaweed" Helv. Chim. Acta 77: 1999-2006. 1994.
Guella et al. "Isolation, Synthesis and Photochemical Properties of Almazolone, a New Indole Alkaloid from a Red Alga of Senegal." Tetrahedron. 62: 1165-1170. 2006.
Harth et al., "An Inhibitor of Exported Mycobacterium Tuberculosis Glutamine Synthetase Selectively Blocks the Growth of Pathogenic Mycobacteria in Axenic Culture and in Human Monocytes: Extracellular Proteins as Potential Novel Drug Targets", J. Exp. Med., 189: 1425-1435. 1999.
Harth et al., "Treatment of Mycobacterium Tuberculosis with Antisense Oligonucleotides to Glutamine Synthetase mRNA Inhibits Glutamine Synthetase Activity, Formation of the Poly-L-Glutamate/Glutamine Cell Wall Structure, and Bacterial Replication", Proc Natl Acad Sci U S A 97:418-423. 2000.
Henderson et al., "Bongkrekic Acid. An Inhibitor of the Adenine Nucleotide Translocase of Mitochondria" J. Biol. Chem. 245: 1319-1326. 1970.
Hirota et al., "Isolation of Indolmycin and its Derivatives as Antagonists of L-Tryptophan" Agri. Biol. Chem. 42: 147-151. 1978.
Holmes et al., "Agricultural Use of Burkholderia (Pseudomonas) Cepacia: A Threat to Human Health?", Emerging Infectious Diseases 4: 221-227. 1998.
Hu et al., "Biocidal Activity in Plant Pathogenic Acidovorax, Burkholderia, Herbaspirillum, Ralstonia, and Xanthomonas spp" J. Appl. Microbiol. 84: 263-271. 1998.
Huss et al., "Studies on the Spectrophotometric Determination of DNA Hybridization from Renaturation Rates" System. Appl. Microbiol. 4: 184-192. 1983.
Janisiewicz et al., "Biological Control of Blue Mold and Gray Mold on Apple and Pear with Pseudomonas Cepacia" Phytopathology 78: 1697-1700. 1988.
Jansen et al., "Thiangazole: a Novel Inhibitor of HIV-1 from Polyangium Spec" Liebigs Ann. Chem. 4: 357-3359. 1992.
Jeong et al., "Toxoflavin Produced by Burkholderia glumae Causing Rice Grain Rot is Responsible for Inducing Bacterial Wilt in Many Field Crops" Plant Disease 87: 890-895. 2003.
Keum et al., "Effects of Nutrients on Quorum Signals and Secondary Metabolite Productions of *Burkholderia* sp O33," J. Microbiology and Biotechnology 19: 1142-1149. 2009.
Knudsen et al., "Field Persistence and Efficacy of Five Bacterial Preparations for Control of Peanut Leaf Spot" Plant Disease 71: 442-445. 1987.
Koga-Ban et al., "cDNA Sequences of Three Kinds of Beta-Tubulins from Rice" DNA Res. 2: 21-26. 1995.
Koyama et al., "Isolation, Characterization, and Synthesis of Pimprinine, Pimprinethine, and Pimprinaphine, Metabolites of Streptoverticillium Olivoreticuli" Agri. Biol. Chem. 45: 1285-1287. 1981.
Krieg et al., "*Bacillus Thuringiensis* Var. *Tenebrionis*: Ein Neuer, Gegenuber Larven von Coleopteren Wirksamer Pathotyp" Z. Angew. Entomol. 96: 500-508. 1983.
Kunze et al., "Thiangazole, a New Thiazoline Antibiotic from Polyangium sp (Myxobacteria): Production, Antimicrobial Activity and Mechanism of Action" J. Antibiot. 46: 1752-1755. 1993.
Lamichhane et al., "Essential Metabolites of Mycobacterium Tuberculosis and their Mimics". mBio 2(1): e00301-10.doi:10.1128/mBio.00301-10. 2011.
Larossa et al., "The Sulfonylurea Herbicide Sulfometuron Methyl is an Extremely Potent and Selective Inhibitor of Acetolactate Synthase in Salmonella Typhimurium", Journal of Biological Chemistry, 259: 8753-8757. 1984.
Lea et al., "The Action of 2-Amino-4-(Methylphosphinyl)-Butanoic Acid (Phosphinothricin) and its 2-Oxo-Derivative on the Metabolism of Cyanobacteria and Higher Plants", Phytochemistry 23: 1-6. 1984.
Lee et al., "Cepacidine A, a Novel Antifungal Antibiotic Produced by Pseudomonas cepacia. 1. Taxonomy, Production, Isolation and Biological Activity", J. Antibiotics 47: 1402-1405. 1994.
Leahy et al., "Comparison of Factors Influencing Trichloroethylene Degradation by Toluene-Oxidizing Bacteria" Appl. Environ. Microbiol. 62: 825-833. 1996.
Lessie et al., "Genomic Complexity and Plasticity of Burkholderia Cepacia" FEMS Microbiol. Lett. 144: 117-128. 1996.
Lindquist et al., "Isolation and Structure Determination of Diazonamides A and B, Unusual Cytotoxic Metabolites from the Marine Ascidian Diazona Chinensis" J. Am. Chem. Soc. 113: 2303-2304. 1991.
Lorch et al., "Basic Methods for Counting Microorganisms in Soil and Water," in *Methods in Applied Soil Microbiology and Biochemistry*. K. Alef and P. Nannipieri. Eds. San Diego, CA, Academic Press: pp. 146-161. 1995.

(56) References Cited

OTHER PUBLICATIONS

Lydon et al., "Inhibitors of Glutamine Biosynthesis", in *Plant Amino Acids: Biochemistry and Biotechnology*. B. Singh, Ed. New York, USA, Marcel Decker. 445-464. 1999.

Mahenthiralingam et al., "DNA-Based Diagnostic Approaches for Identification of Burkholderia Cepacia Complex, Burkholderia Vietnamiensis, Burkholderia Multivorans, Burkholderia Stabilis, and Burkholderia Cepacia Genomovars I and III" J. Clin. Microbiol. 38: 3165-3173. 2000.

Mao et al., "Isolation and Characterization of Antifungal Substances from Burkholderia sp Culture Broth", Current Microbiology, 53: 358-364. 2006.

Meyers et al., "Xylocandin: A New Complex of Antifungal Peptides. 1.Taxonomy, Isolation and Biological Activity", J. Antibiotics, 40: 1515-1519. 1987.

Ming et al., "Metal Binding and Structure-Activity Relationship of the Metalloantibiotic Peptide Bacitracin" J. Inorganic Biochemistry 91: 46-58. 2002.

Moon et al., "Plant Growth Promoting and Fungicidal 4-Quinolinones from Pseudomonas Cepacia", Phytochemistry, 42: 365-368. 1996.

Morita et al., "Biological Activity of Tropolone" Biol. Pharm. Bull. 26: 1487-1490. 2003.

Nagamatsu, "Syntheses, Transformation, and Biological Activities of 7-Azapteridine Antibiotics: Toxoflavin, Fervenulin, Reumycin and their Analogs" Recent Res. Devel. Org. Bioorg. Chem. 4: 97-121. 2001.

Naik, et al., "Pimprinine, an Extracellular Alkaloid Produced by Streptomyces CDRIL-312: Fermentation, Isolation and Pharmacological Activity" J. Biotech. 88: 1-10. 2001.

Nakajima et al., "Hydantocidin: a New Compound with Herbicidal Activity" J. Antibiot. 44: 293-300. 1991.

Nakajima et al., "New Antitumor Substances, FR901463, FR901464 and FR901465. I. Taxonomy, Fermentation, Isolation, Physico-Chemical Properties and Biological Activities" J. Antibiot. 49: 1196-1203. 1996.

Nakajima et al., "New Antitumor Substances, FR901463, FR901464 and FR901465. II. Activities Against Experimental Tumors in Mice and Mechanism of Action" J. Antibiot. 49: 1204-1211. 1996.

N'Diaye et al., "Almazole A and Almazole B, Unusual Marine Alkaloids of an Unidentified Red Seaweed of the Family Delesseriaceae from the Coasts of Senegal" Tet. Lett. 35: 4827-4830. 1994.

N'Diaye et al., "Almazole D, a New Type of Antibacterial 2,5-Disubstituted Oxazolic Dipeptide from a Red Alga of the Coast of Senegal" Tet. Lett. 37: 3049-3050. 1996.

Nierman et al., "Structural Flexibility in the Burkholderia Mallei Genome" Proc. Natl. Acad. Sci. USA 101: 14246-14251. 2004.

Okazaki et al., "Rhizobial Strategies to Enhance Symbiotic Interaction: Rhizobitoxine and 1-Aminocyclopropane-1-Carboxylate Deaminase" Microbes Environ. 19: 99-111. 2004.

Parke et al., "Diversity of the Burkholderia Cepacia Complex and Implications for Risk Assessment of Biological Control Strains" Annu. Rev. in Phytopathology 39: 225-258. 2001.

Partida-Martinez et al., "A Gene Cluster Encoding Rhizoxin Biosynthesis in 'Burkholderia Rhizoxina,' the Bacterial Endosymbiont of the Fungus Rhizopus Microsporus", ChemBioChem, 8: 41-45. 2007.

Petit et al. "Isolation of Labradorins 1 and 2 from Pseudomonas Syringae pv. corona faciens" J. Nat. Prod. 65: 1793-1797. 2002.

Pitt et al., "Type Characterization and Antibiotic Susceptibility of Burkholderia (Pseudomonas) Cepacia Isolates from Patients with Cystic Fibrosis in the United Kingdom and the Republic of Ireland" J. Med. Microbiol. 44: 203-210. 1996.

Ramette et al., "Species Abundance and Diversity of Burkholderia Cepacia Complex in the Environment" Appl. Environ. Microbiol. 71: 1193-1201. 2005.

Reis et al., "*Burkholderia tropica* sp. nov., a Novel Nitrogen-Fixing, Plant-Associated Bacterium" Int. J. Syst. Evol. Microbiol. 54: 2155-2162. 2004.

Salama et al., "Potency of Spore-γ-Endotoxin Complexes of Bacillus Thuringiensis Against Some Cotton Pests" Z. Angew. Entomol. 91: 388-398. 1981.

Selva et al., "Targeted Screening for Elongation Factor Tu Binding Antibiotics" J. Antibiot. 50: 22-26. 1997.

Selvakumar et al., "Production and Bioassay of Bialaphos Biosynthesized by Streptomyces Hydroscopicus NRRL B-16256," Bioprocess Engineering 20:459-462. 1999.

Shao et al., "Biosynthesis of 2-Hydroxyethyl phosphate, an Unexpected Intermediate Common to Multiple Phosphonate Biosynthetic Pathways," J. Biol. Chem. 283:23161-23168. 2008.

Shoji et al., "Isolation of Cepafungins I, II and III from Pseudomonas Species", J. Antibiotics, 43, 783-787. 1990.

Singh et al., "Development of a Simple Assay Protocol for High-Throughput Screening of Mycobacterium Tuberculosis Glutamine Synthetase for the Identification of Novel Inhibitors", Journal of Biomolecular Screening, 10(7): 725-729. 2005.

Singh et al., "Development of a Simple High-Throughput Screening Protocol Based on Biosynthetic Activity of Mycobacterium Tuberculosis Glutamine Synthetase for the Identification of Novel Inhibitors", J Biomol Screen11: 1035-1042. 2006.

Schweizer, et al., "Mechanisms of antibiotic resistance in Burkholderia pseudomallei: implications for treatment of melioidosis", Future Microbiolo., Dec. 2012, vol. 7. No. 12, pp. 1389-1399.

Stokell, et al., Rapid emergence of a ceftazidime-resistant Burkholderia multivorans strain in a cystic fibrosis patient, J. Cyst. Fibros., Mar. 9, 2013. vol. 12 No. 6, pp. 812-816.

Spilker et al., "PCR-Based Assay for Differentiation of Pseudomonas Aeruginosa from other Pseudomonas Species Recovered From Cystic Fibrosis Patients" J. Clin. Microbiol. 42: 2074-2079. 2004.

Stead et al., "Induction of Phenazine Biosynthesis in Cultures of Pseudomonas Aeruginosa by L-N-(3-oxohexanoyl) Homoserine Lactone" FEMS Microbio. Letters 140:15-22. 1996.

Sultan et al., "Novel Oxidized Derivatives of Antifungal Pyrrolnitrin from the Bacterium Burkholderia Cepacia K87," J. Antibiotics 61: 420-425. 2008.

Tachibana et al., "Inhibition of Glutamine Synthetase and Quantitative Changes of Free Amino Acids in Shoots of Bialaphos Treated Japanese Barnyard Millet", J. Pesticide Science, 11:27-31. 1986.

Takahashi et al., "Martefragin A, a Novel Indole Alkaloid Isolated from a Red Alga, Inhibits Lipid Peroxidation" Chem Pharm. Bull. 46: 1527-1529. 1998.

Takita et al., "Chemistry of Bleomycin. XIX Revised Structures of Bleomycin and Phleomycin" J. Antibiot. 31: 801-804. 1978.

Thompson et al., "Spinosad—A Case Study: An Example from a Natural Products Discovery Programme" Pest Management Sci. 56: 696-702. 2000.

Tran Van et al., "Repeated Beneficial Effects of Rice Inoculation with a Strain of Burkholderia Vietnamiensis on Early and Late Yield Component in Low Fertility Sulphate Acid Soils of Vietnam" Plant and Soil 218: 273-284. 2000.

Tsuruo et al., "Rhizoxin, a Macrocyclic Lactone Antibiotic, as a New Antitumor Agent Against Human and Murine Tumor Cells and their Vincristine-Resistant Sublines" Cancer Res. 46: 381-385. 1986.

Umehara et al., "Studies of New Antiplatelet Agents WS-30581 A and B" J. Antibiot. 37: 1153-1160. 1984.

Ueda et al., "FR901228, a Novel Antitumor Bicyclic Depsipeptide Produced by Chromobacterium violaceum No. 968," J. Antibiotics 47:301-310. 1994.

Vandamme et al. "Polyphasic Taxonomic Study of the Emended Genus *Arcobacter* with *Arcobacter butzleri* comb. nov. and *Arcobacter skirrowii* sp. nov., an Aerotolerant Bacterium Isolated from Veterinary Specimens" Int. J. Syst. Bacteriol. 42: 344-356. 1992.

Vanderwall et al., "A Model of the Structure of HOO-Co Bleomycin Bound to d(CCAGTACTGG): Recognition at the d(GpT)site and Implications for Double-Stranded DNA Cleavage" Chem. Biol. 4: 373-387. 1997.

Vencill et al., "Herbicide Resistance: Toward an Understanding of Resistance Development and the Impact of Herbicide-Resistant Crops", Weed Science. 60: 2-30. 2012.

(56) References Cited

OTHER PUBLICATIONS

Vermis et al. "Evaluation of Species-Specific RecA-Based PCR Tests for Genomovar Level Identification Within the Burkholderia Cepacia Complex" J. Med. Microbiol. 51: 937-940. 2002.
Vial et al., "Burkholderia Diversity and Versatility: An Inventory of the Extracellular Products", J. Microbiol. Biotechnol. 17:9. 1407-1429. 2007.
Watanabe et al, "A New Antibiotic SF2583A, 4-Chloro-5-(3'indoly)oxazole, Produced by Streptomyces" Meiji Seika Kenkyu Nenpo 27: 55-62. 1988.
Wayne et al., "Report of the Ad Hoc Committee on Reconciliation of Approaches to Bacterial Systematics" Int. J. Syst. Bacteriology. 37: 463-464. 1987.
Werner et al., "Uptake of Indolmycin in Gram-positive Bacteria." Antimicrob. Agents Chemotherapy 18: 858-862. 1980.
Wilson et al., "Toxicity of Rhizonin A, Isolated from Rhizopus Microsporus, in Laboratory Animals" Food Chem. Toxicol. 22: 275-281. 1984.
Zeck, "A Rating System for Field Evaluation of Root-Knot Nematode Infestations," Pflanzenschutz-Nachrichten Bayer 24,1: 141-144. 1971.
Zhou et al., "Antimicrobial Susceptibility and Synergy Studies of Burkholderia Cepacia Complex Isolated From Patients with Cystic Fibrosis" Antimicrob. Agents and Chemotherapy 51: 1085-1088. 2007.
Extended European Search Report for EP App. No. 11748040.0 dated Jun. 5, 2013.
International Search Report and Written Opinion for Application No. PCT/US2011/026016 dated Jan. 18, 2012.
International Preliminary Report on Patentability for Application No. PCT/US2011/0260126 dated Aug. 28, 2012.
International Search Report and Written Opinion for Application No. PCT/US2012/050807 dated Feb. 26, 2013.
International Search Report and Written Opinion for Application No. PCT/US2014/015799 dated May 27, 2014.
Database EMBL Accession No. AF148554, Jun. 7, 2000.
Database EMBL Accession No. AF265235, Jun. 8, 2001.
Database EMBL Accession No. AB092606, Apr. 2, 2003.
Database EMBL Accession No. AJ420880, Nov. 27, 2001.
Database EMBL Accession No. AF175314, Sep. 5, 2000.
Database EMBL Accession No. AM905038, Nov. 20, 2007.
Database EMBL Accession No. AY740337, Oct. 10, 2004.
Database EMBL Accession No. AB212236, Mar. 28, 2006.
Database EMBL Accession No. AB212227, Mar. 28, 2006.
Database EMBL Accession No. AY741345 Oct. 10, 2004.
Database EMBL Accession No. AB508854, Jul. 2, 2009.
Database EMBL Accession No. AY741351, Oct. 10, 2004.
Database EMBL Accession No. AY741349, Oct. 10, 2004.
Database EMBL Accession No. AY40350, Aug. 31, 2005.
Database EMBL Accession No. AY741334, Oct. 10, 2004.
Database EMBL Accession No. AY741348, Oct. 10, 2004.
Database EMBL Accession No. AY741330, Oct. 10, 2004.
Database EMBL Accession No. AY741340, Oct. 10, 2004.
Database EMBL Accession No. AY741339, Oct. 10, 2004.
Database EMBL Accession No. AM747631, Jun. 27, 2007.
Database EMBL Accession No. AY741359, Oct. 10, 2004.
Database EMBL Accession No. AY741341, Oct. 10, 2004.
Database EMBL Accession No. AY741353, Oct. 10, 2004.
Database EMBL Accession No. AM747632, Jun. 21, 2007.
Database EMBL Accession No. AM747628, Jun. 21, 2007.
Database EMBL Accession No. AY661910, Aug. 3, 2004.
Database EMBL Accession No. FJ932759, Jun. 3, 2009.
Database EMBL Accession No. AM747630, Jun. 21, 2007.
Database EMBL Accession No. EU684748, Jun. 8, 2008.
Database EMBL Accession No. AB021369, Jan. 22, 1999.
Database EMBL Accession No. AY741361, Oct. 10, 2004.
Database EMBL Accession No. AY741335, Oct. 10, 2004.
Database EMBL Accession No. AB211225, Apr. 16, 2005.
Database EMBL Accession No. FJ436055, Dec. 29, 2008.
Database EMBL Accession No. DQ273265, Dec. 7, 2005.
Database EMBL Accession No. GQ359110, Aug. 16, 2009.
Database EMBL Accession No. U96927, Jul. 1, 1998.
Database EMBL Accession No. EU826644, Nov. 3, 2008.
Database EMBL Accession No. E10021, Oct. 8, 1997.
Database EMBL Accession No. AB252073, Aug. 29, 2006.
Database EMBL Accession No. U96928, Jul. 1, 1998.
Database EMBL Accession No. EU305400, Jan. 8, 2008.
Database EMBL Accession No. FJ870663, May 10, 2009.
Database EMBL Accession No. AY662003, Aug. 3, 2004.
Database EMBL Accession No. AJ491304, Jun. 17, 2003.
Database EMBL Accession No. U96937, Jul. 1, 1998.
Database EMBL Accession No. U96929, Jul. 1, 1998.
Database EMBL Accession No. FJ606689, Jan. 20, 2009.
Database EMBL Accession No. AY946011, Mar. 26, 2005.
Database EMBL Accession No. EU214612, Jul. 8, 2008.
Database EMBL Accession No. AY946010, Mar. 26, 2005.

* cited by examiner

Templazole A (i)

Templazole B (ii)

FR 901228 (iii)

Note: X= 5 when samples are drawn from 96 well plate with multiple channel pipette, but X=1 when samples are drawn from individual vials with a syringe.

PLANT GLUTAMINE SYNTHETASE INHIBITORS AND METHODS FOR THEIR IDENTIFICATION

SEQUENCE LISTING

The instant application contains a Sequence Listing which has been submitted in ASCII format via EFS-Web and is hereby incorporated by reference in its entirety. Said ASCII copy, is named MOI-42037-US-SEQ.txt and is 16 kB in size.

TECHNICAL FIELD

Provided are methods for identification of plant glutamine synthetase inhibitors as well as the plant synthetase inhibitors identified. Also provided are methods of use of plant glutamine synthetase inhibitors or substances comprising such inhibitors for modulating glutamine synthetase in a plant and particularly a weed.

BACKGROUND

Modern farming and plant production require a constant string of new and novel means of controlling weeds and other pests. Fields are treated with herbicides to rid them of unwanted plants, allowing efficient production of useful crops. Over generations, however, these unwanted plants naturally develop resistance to the standard arsenal of herbicides. New and novel herbicides are constantly required in order to maintain and improve crop yields, such that people are sufficiently fed and clothed.

Herbicides work through modulation of various physiological functions of plant growth. Modulations in the physiological functions that affect plant growth, development, seasonality, dormancy and reproduction. This damage weakens a plant and occasionally results in death. Many types of damage can be compensated for, such that plants survive despite this damage. However, modulation of particularly critical physiological functions will directly affect a plant's survivability. The nature of these modulations is the basis of commercial herbicide development.

Most commercial herbicides modulate one of the critical physiological functions for plant life such as pigment synthesis, plant root/shoot growth, lipid biosynthesis, photosynthesis, respiration, plant auxin, auxin transporter, cell division, cellulose synthesis, amino acid synthesis and so on. Many of these physiological functions can be inhibited by multiple classes of herbicides. For example, imidazolinones, pyrimidinylthiobenzoate, sulfonylamino-carbonyltriazolinones, sulfonlyureas, and triazolopyrimidines are herbicides that inhibit acetolactate synthesis (ALS), a key enzyme in the biosynthesis of branched amino acids such as isoleucine, leucine and valine (LaRossa and Schloss, 1984). Other examples are phenylcarbamates, pyridazinones, triazinones, uracils, amides, ureas, benzothiadiazinones, nitriles, and phenylpyridazines that are herbicides that inhibit photosynthesis by binding to the $Q_B$-binding niche on the D1 protein of photosynthesis II complex in chloroplast thylakoid membranes (Vencill et al., 2012).

Glutamine Synthetase

Glutamine synthetase is a key enzyme in facilitating the condensation of glutamate and ammonium to form glutamine and thus plays a significant role in the metabolism of ammonia in both prokaryotic and eukaryotic cells (reviewed in Eisenberg, 2000).

Extracellular glutamate synthetase has been found to play a significant role in the survival of *Mycobacterium tuberculosis* (see, for example, Harth et al., 2000). Inhibitors of glutamine synthetase such as L-Methionine sulfoximine and JFD01307SC directed towards *M. tuberculosis* (Lamichhane et al., 2011) and screening methods for their detection have been developed (see, for example, Singh et al., 2005, 2006, US Patent Appln. Pub. No. 20100022584).

Plant glutamine synthetase (GS) has been found to play a critical role in ammonia metabolism in plants as well (see, for example, Castro-Rodríguez, et al., 2011). It has been found to exist in two isoforms, cytosolic and plastidic.

Inhibiting glutamine synthetase (GS) is one mechanism of action for controlling weeds. Currently, there is only one class of commercial herbicides that has been developed for inhibiting GS, using a key enzyme converting glutamate and ammonium into glutamine (Lea 1984). Phosphinic acids (glufosinate and bialaphos) inhibit the activity of GS, resulting in an accumulation of ammonium in plants (Tachibana 1986). The ammonia destroys the cells and directly inhibits photosynthesis I and II reactions (Vencill et al., 2012) by reducing the pH gradient across the membrane which can uncouple photophosphorylation.

Glufosinate or phosphinothricin is a commercial synthesized product; it is a racemic version of DL-glufosinate-ammonium salt. Glufosinate is sold under trade names Basta, Buster and Liberty.

Bialaphos is a naturally occurring tripeptide herbicide that comes from a soil microorganism, *Streptomyces hygroscopicus* [Selvakumar et al., 1999]. It is also produced by *S. viridochromeogenes* (Krainsky) [Blodgett et al., 2008]. Bialaphos is a proherbicide, which has to be metabolized into a phytotoxin: phosphinothricin {4-[hydroxyl(methyl)phosphinoyl]-L-homoalanine]. Phosphinothricin is an irreversible inhibitor of GS. Bialaphos was introduced in Japan in 1984 and it was the first herbicide produced by fermentation. It is commercially available.

One of the strengths of GS inhibition is that crops have been genetically engineered for resistance to the compounds when used as herbicides. Glufosinate or its ammonium salt DL-phosphinothricin is an active ingredient in several non-selective systemic herbicides such as BASTA®, RELY®, FINALE®, IGNITE®, CHALLENGE®, AND LIBERTY®. Bayer Company has marketed such crops under the LIBERTY LINK® trademark to be used with their glufosinate herbicide. Glufosinate-treated plants die due to a buildup of ammonia and a cessation of photosynthesis due to lack of glutamine.

Burkholderia

The bacterial species in the genus *Burkholderia* are ubiquitous in soil, rhizosphere, insects, fungus and water (Coenye and Vandamme, 2003; Parke and Gurian-Sherman, 2001). The *Burkholderia* genus, β-subdivision of the proteobacteria, comprises more than 40 species that inhabit diverse ecological niches (Compant et al. 2008). Traditionally, they have been known as plant pathogens, *B. cepacia* being the first one discovered and identified as the pathogen causing disease in onions (Burkholder, 1950). Several *Burkholderia* species have developed beneficial interactions with their plant hosts (see, for example, Cabballero-Mellado et al., 2004, Chen et al., 2007). Some *Burkholderia* species have also been found to be opportunistic human pathogens; see, for example, Cheng and Currie, 2005 and Nierman et al., 2004. Additionally, some *Burkholderia* species have been found to have potential as biocontrol products (see for example, Burkhead et al., 1994; Knudsen et al., 1987; Jansiewicz et al., 1988; Gouge et al., US20030082147; Parke, U.S. Pat. No. 6,077,505; Cassida, U.S. Pat. No. 6,689,357; Jeddeloh et al., WO2001055398; Zhang et al., U.S. Pat. No. 7,141,407).

Some species of in this genus have been effective in bioremediation to decontaminate polluted soil or groundwater (see, for example, Leahy et al. 1996; Lessie et al. 1996). Further, some *Burkholderia* species have been found to secrete a variety of extracellular enzymes with proteolytic, lipolytic and hemolytic activities, as well as toxins, antibiotics, and siderophores (see, for example, Ludovic et al., 2007; Nagamatsu, 2001; Morita et al., 2003; Okazaki et al., 2004).

Known Secondary Metabolites from *Burkholderia*

In a recent review, (Vial et al., 2007) there is discussion of the great diversity and versatility of extracellular compounds produced by the different species of *Burkholderia* sp. Some of the known toxins produced by *Burkholderia* sp. include a) toxoflavin (1,6-dimethylpyrimido[5,4-e]-1,2,4-triazine-5,7 (1H, 6H)-dione) and fervenulin (a tautomeric isomer of toxoflavin) with antibacterial, antifungal, and herbicidal activities (Jeong, et al., 2003); b) tropolone (2-hydroxy-2,4,6-cycloheptatrien-1-one), a non-benzenoid aromatic compound with both phenolic and acidic moieties and proven antimicrobial, antifungal, and insecticidal properties (Okazaki et al., 2004); c) rhizobitoxin ([2-amino-4-(2-amino-3-hydroxypropoxy)-trans-but-3-enoic-acid]), that, among other phytotoxic effects, induced foliar chlorosis due to inhibition of cystathione-β-lyase (Morita et al., 2003); d) rhizoxin, a macrocyclic polyketide, which kills rice seedlings by binding to β-tubulin, inhibiting the normal cell division cycle (Koga-Ban et al., 1995) and demonstrating broad antitumor activity in vitro (Tsuruo et al., 1986); e) bongkrekic acid, which inhibits adenine nucleotide translocase as well as cell apoptosis (Henderso et al., 1970); and f) rhizonin A and B, hepatotoxic cyclopeptides that were first discovered from a fungus (*Rhizopus* sp.) but later were shown to be produced by a bacterial endosymbiont of the genus *Burkholderia* (Partida-Martinez et al., 2007).

One of the best characterized antimicrobial and antifungal compounds produced by *Burkholderia* sp., are cepaciamide (Holmes et al., 1998); cepacidine A (Lee et al., 1994) and related compounds in the xylocandin complex (Meyers et al., 1987); pyrrolnitrin (Burkhead et al 1997; El-Banna et al., 1998) and its derivatives (Sultan et al., 2008) pseudanes (Moon et al., 1996), phenazine (Stead et al., 1996) maculosin and banegasine (Cain et al., 2003); glidobactins such as cepafungin (Shoji et al., 1990); phenylacetic acid, hydrocinnamic acid, 4-hydroxyphenylacetic acid, and 4-hydroxyphenylacetate methyl ester (Mao et al., 2006). Other antifungal compounds summarized by Vial et al. (2007) include 2-hydroxymethyl-chroman-4-one, oligopeptides called altericidins, capacins A and B, hydrogen cyanide and a wide variety of volatile small molecules. Several *Burkholderia* strains are also known to produce phytohormones and siderophores such as pyochelin, ornibactin, malleobactin, capabactin, cepaciachelin, effector proteins as well as surface-active glycolipids called rhamnolipids (Abdel-Mawgoud et al., 2010). As in several Gram-negative bacteria, the production of most of the above mentioned secondary metabolites is mediated through N-acylhomoserine lactone (AHSL or AHL) by a process known as quorum sensing (QS; (Keum et al., 2009)). Quorum sensing is a cell-to-cell communication system that perceives and responds to population density in order to coordinate gene expression (Vial et al., 2007). It appears to be present in every *Burkholderia* strain studied so far (Deng et al., 2010).

Oxazoles, Thiazoles and Indoles

Oxazoles, thiazoles and indoles are widely distributed in plants, algae, sponges, and microorganisms. A large number of natural products contain one or more of the five-membered oxazole, thiazole and indole nucleus/moieties. These natural products exhibit a broad spectrum of biological activity with demonstrable therapeutic value. For example, bleomycin A (Tomohisa et al.), a widely prescribed anticancer drug, effects the oxidative degradation of DNA and uses a bithiazole moiety to bind its target DNA sequences (Vanderwall et al., 1997). Bacitracin (Ming et al., 2002), a thiazoline-containing peptide antibiotic, interdicts bacterial cell wall new biosynthesis by complexation with C55-bactoprenolpyrophosphate. Thiangazole (Kunze et al., 1993) contains a tandem array of one oxazole and three thiazolines and exhibits antiviral activity (Jansen et al., 1992). Other oxazole/thiazole-containing natural products such as thiostrepton (Anderson et al., 1970) and GE2270A (Selva et al., 1997) inhibit translation steps in bacterial protein synthesis. More than 1000 alkaloids with the indole skeleton have been reported from microorganisms. One-third of these compounds are peptides with masses beyond 500 Da where the indole is tryptophan derived. The structural variety of the remaining two-thirds is greater and their biological activity appears to cover a broader range, including antimicrobial, antiviral, cytotoxic, insecticidal, antithrombotic, and enzyme inhibitory activity.

SUMMARY OF DISCLOSURE

Provided is a method for modulating glutamine synthetase activity in a plant in need thereof comprising applying to the plant or substrate for growing said plant an amount of an isolated culture of a microorganism strain or supernatant or extract of said microorganism effective to modulate said glutamine synthetase activity and in a particular embodiment systemically modulating growth of a plant, particularly, a weed. In a particular embodiment the culture is an inactivated culture.

Provided in particular is a method for modulating glutamine synthetase activity in a plant in need thereof comprising applying to the plant or substrate for growing said plant an amount of (A) an isolated live or inactivated culture of a isolated strain of a non-*Burkholderia cepacia*, non-*Burkholderia plantari*, non-*Burkholderia gladioli*, *Burkholderia* sp. non-*Burkholderia cepacia*, non-*Burkholderia multivorans*, *Burkholderia* sp. or cell fraction, supernatant, extract or compound that modulates glutamine synthetase activity in a plant, derived from said inactivated culture, wherein said *Burkholderia* strain prior to inactivation of said culture has the following characteristics:

(1) a 16S rRNA gene sequence comprising the forward sequence having at least 99% identity to the sequence set forth in SEQ ID NO:8, 11, 12 and a reverse sequence having at least 99% identity to the sequence set forth in SEQ ID NO:9, 10, 13, 14 and 15;

(2) pesticidal activity;

(3) produces a pesticidal compound selected from the group consisting of:

(i) a compound having the following properties: (a) a molecular weight of about 525-555 as determined by Liquid Chromatography/Mass Spectroscopy (LC/MS); (b) $^1$H NMR values of 6.22, 5.81, 5.69, 5.66, 5.65, 4.64, 4.31, 3.93, 3.22, 3.21, 3.15, 3.10, 2.69, 2.62, 2.26, 2.23. 1.74, 1.15, 1.12, 1.05, 1.02; (c) has $^{13}$C NMR values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51 and (c) an High Pressure Liquid Chromatography (HPLC) retention time of about 10-15 minutes, on a reversed phase C-18 HPLC column using a water:acetonitrile ($CH_3CN$) gradient;

(ii) a compound having an oxazolyl-indole structure comprising at least one indole moiety, at least one oxazole moiety, at least one substituted alkyl group and at least one carboxylic ester group; at least 17 carbons and at least 3 oxygen and 2 nitrogens;

(iii) a compound having an oxazolyl-benzyl structure comprising at least one benzyl moiety, at least one oxazole moiety, at least one substituted alkyl group and at least one amide group; at least 15 carbons and at least 2 oxygen and 2 nitrogens (B) optionally another substance, wherein said substance is an herbicidal substance in amounts effective to modulate said glutamine synthetase activity of said plants. In a particular embodiment, the substance systemically modulates the growth of the plant.

The compound used in the method set forth above may be selected from the group consisting of:

(i) a compound having the following properties: (a) a molecular weight of about 525-555 as determined by Liquid Chromatography/Mass Spectroscopy (LC/MS); (b) 1H NMR values of 6.22, 5.81, 5.69, 5.66, 5.65, 4.64, 4.31, 3.93, 3.22, 3.21, 3.15, 3.10, 2.69, 2.62, 2.26, 2.23. 1.74, 1.15, 1.12, 1.05, 1.02; (c) has $^{13}C$ NMR values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51 and (c) a High Pressure Liquid Chromatography (HPLC) retention time of about 10-15 minutes, on a reversed phase C-18 HPLC column using a water:acetonitrile ($CH_3CN$) gradient;

(ii) a compound having an oxazolyl-indole structure comprising at least one indole moiety, at least one oxazole moiety, at least one substituted alkyl group and at least one carboxylic ester group; at least 17 carbons and at least 3 oxygen and 2 nitrogens;

(iii) a compound having an oxazolyl-benzyl structure comprising at least one benzyl moiety, at least one oxazole moiety, at least one substituted alkyl group and at least one amide group; at least 15 carbons and at least 2 oxygen and 2 nitrogens.

The compound used in the method set forth above may selected from the group consisting of (i) templazole A; (ii) templazole B and (iii) FR901228. In a particular embodiment, the plant is a weed.

Also provided is a composition comprising an isolated inactivated or living culture of an isolated strain of a non-*Burkholderia cepacia*, non-*Burkholderia plantari*, non-*Burkholderia gladioli*, *Burkholderia* sp. non-*Burkholderia cepacia*, non-*Burkholderia multivorans*, *Burkholderia* sp. or cell fraction, supernatant, extract or compound derived from said inactivated culture. Further provided is a combination comprising said composition or said inactivated or living culture of an isolated strain of a non-*Burkholderia cepacia*, non-*Burkholderia plantari*, non-*Burkholderia gladioli*, *Burkholderia* sp. non-*Burkholderia cepacia*, non-*Burkholderia multivorans*, *Burkholderia* sp. or cell fraction, supernatant, extract or compound derived from said inactivated culture and a pesticidal and particularly an herbicidal substance.

Further provided is a method for modulating the growth and/or emergence of monocotyledonous and/or dicotyledonous weeds comprising applying to the weed or substrate where said weed emerges or grows an amount of the composition or combination set forth above effective to modulate said growth or emergence. In a particular embodiment, the effect of said substance is systemic.

Also provided is a method for identifying a substance that modulates and, in a particular embodiment, inhibits plant glutamine synthetase activity in vitro comprising: (a) contacting a plant glutamine synthetase polypeptide with a test plant glutamine synthetase inhibitor and (b) determining whether or not the activity of the glutamine synthetase is modulated or, in a particular embodiment, reduced relative to the activity of the glutamine synthetase polypeptide that has not been contacted with the test glutamine synthetase inhibitor. The method may further comprise comparing the activity of the glutamine synthetase when contacted with a test plant glutamine synthetase inhibitor to the activity of the glutamine synthetase when contacted with a known plant glutamine synthetase modulator and, in a particular embodiment, inhibitor. This method may further be used to identify herbicidal substances by (a) identifying a substance that inhibits plant glutamine synthetase activity according to the method set forth above and (b) determining if said substance identified as a glutamine synthetase inhibitor in (a) has herbicidal activity.

DETAILED DESCRIPTION OF EMBODIMENTS

Figure 1:
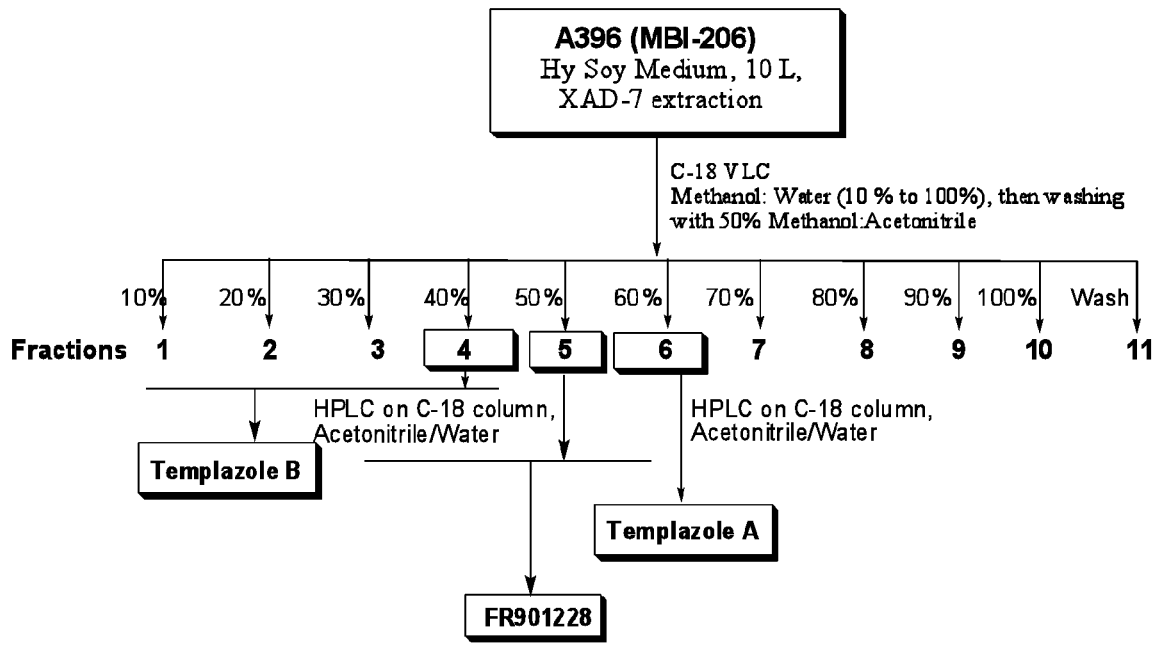
FIG. 1 show the general scheme used to obtain fractions from the MBI-206 fermentation broth.
Figure 2:
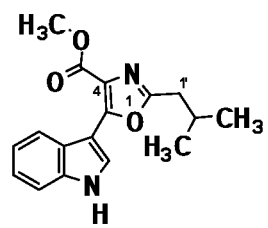
FIG. 2 depicts the structure for the active compounds.
Figure 2:
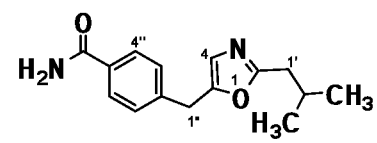
Figure 2:
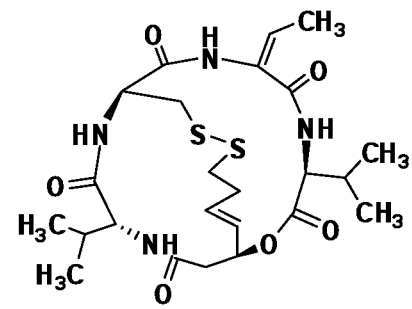

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As used herein, "derived from" means directly isolated or obtained from a particular source or alternatively having identifying characteristics of a substance or organism isolated or obtained from a particular source. A substance obtained via recombinant DNA methods may also be considered to be "derived from" a particular source.

As used herein, a substance, compound or microorganism is "isolated" if it is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods.

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As used herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl-, wherein alkyl is as defined above, and "substituted alkoxy" refers to alkoxyl groups further bearing one or more substituents as set forth above.

As used herein, "thioalkyl" refers to the moiety —S-alkyl-, wherein alkyl is as defined above, and "substituted thioalkyl" refers to thioalkyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituent's as set forth above.

As used herein, "modulate" refers to altering the amount or rate of production of or Km of "glutamine synthetase"

As used herein "inactivated" means that the *Burkholderia* cells in culture are unable to grow after said activated treatment.

Substance Responsible for Modulating Glutamine Synthetase (GS) Activity

Provided are substances responsible for modulating glutamine synthetase activity. In a particular embodiment, these substances inhibit glutamine synthetase activity at least about 30%, more particularly, at least about 40% and most particularly at least about 50%.

In a particular embodiment, the substance is an isolated or substantially pure culture or whole cell broth comprising or a fraction, supernatant, cells or extract derived from an isolated inactivated or living culture of a *Burkholderia* strain, which in a particular embodiment is described in US Patent Appln. Pub. No. US20110207604A1. The culture may be inactivated by heat treatment or by chemical treatment, such as with an alcohol. In a particular embodiment, the culture is inactivated by heat treatment for a time and under conditions sufficient so that a culture of the *Burkholderia* is unable to grow under routine culture conditions.

The *Burkholderia* strain set forth herein is a non-*Burkholderia cepacia* complex, non-*Burkholderia plantari*, non-*Burkholderia gladioli, Burkholderia* sp and non-pathogenic to vertebrates, such as birds, mammals and fish. This strain may be isolated from a soil sample using procedures known in the art and described by Lorch et al., 1995. The *Burkholderia* strain may be isolated from many different types of soil or growth medium. The sample is then plated on potato dextrose agar (PDA). The bacteria are gram negative, and it forms round, opaque cream-colored colonies that change to pink and pinkish-brown in color and mucoid or slimy over time.

Colonies are isolated from the potato dextrose agar plates and screened for those that have biological, genetic, biochemical and/or enzymatic characteristics of the *Burkholderia* strain of the present invention set forth in the Examples below. In particular, the *Burkholderia* strain has a 16S rRNA gene comprising a forward sequence that is at least about 99.5%, more preferably about 99.9% and most preferably about 100% identical to the sequence set forth in SEQ ID NO: 8, 11 and 12 and a forward sequence that is at least about 99.5%, more preferably about 99.9% and most preferably about 100% identical to the sequence set forth in SEQ ID NO: 9, 10, 13, 14 and 15 as determined by clustal analysis. Furthermore, as set forth below, this *Burkholderia* strain may before inactivation, as set forth below, have pesticidal activity, particularly, virucidal, herbicidal, germicidal, fungicidal, nematicidal, bactericidal and insecticidal and more particularly, herbicidal, algicidal, acaricidal, insecticidal, fungicidal and nematicidal activity. It is not pathogenic to vertebrate animals, such as mammals, birds, and fish.

Additionally, the *Burkholderia* strain produces at least the pesticidal compounds set forth in the instant disclosure.

The *Burkholderia* strain is susceptible to kanamycin, chloramphenicol, ciprofloxacin, piperacillin, imipenem, and a combination of sulphamethoxazole and trimethoprim and contains the fatty acids 16:0, cyclo 17:0, 16:0 3-OH, 14:0, cyclo 19:0, 18:0.

This *Burkholderia* strain may be obtained by culturing a microorganism having the identifying characteristics of *Burkholderia* A396 (NRRL Accession No. B-50319) on Potato Dextrose Agar (PDA) or in a fermentation medium containing defined carbon sources such as glucose, maltose, fructose, galactose, and undefined nitrogen sources such as peptone, tryptone, soytone, and NZ amine.

The GS modulating compounds disclosed herein may have the following properties: (a) is obtainable from an inactivated/living culture of, or supernatant, extract or fraction of said inactivated/living culture of a *Burkholderia* species, e.g., A396; (b) have herbicidal activity; (c) has a molecular weight of about 525-555 and more particularly, 540 as determined by Liquid Chromatography/Mass Spectroscopy (LC/MS); (d) has $^{1}H$ NMR values of 6.22, 5.81, 5.69, 5.66, 5.65, 4.64, 4.31, 3.93, 3.22, 3.21, 3.15, 3.10, 2.69, 2.62, 2.26, 2.23. 1.74, 1.15, 1.12, 1.05, 1.02; (d) has $^{13}C$ NMR values of 172.99, 172.93, 169.57, 169.23, 167.59, 130.74, 130.12, 129.93, 128.32, 73.49, 62.95, 59.42, 57.73, 38.39, 38.00, 35.49, 30.90, 30.36, 29.26, 18.59, 18.38, 18.09, 17.93, 12.51; (e) has a High Pressure Liquid Chromatography (HPLC) retention time of about 10-15 minutes, more specifically about 12 minutes and even more specifically about 12.14 min on a reversed phase C-18 HPLC (Phenomenex, Luna 5μ C18 (2) 100 A, 100×4.60 mm) column using a water:acetonitrile ($CH_3CN$) with a gradient solvent system (0-20 min 90-0% aqueous $CH_3CN$, 20-24 min 100% $CH_3CN$, 24-27 min, 0-90% aqueous $CH_3CN$, 27-30 min 90% aqueous $CH_3CN$) at 0.5 mL/min flow rate and UV detection of 210 nm; (f) has a molecular formula, $C_{24}H_{36}N_4O_6S_2$, which is determined by interpretation of $^1H$, $^{13}C$ NMR and LC/MS data; (g) a $^{13}C$ NMR spectrum with signals for all 24 carbons, including 5 methyl, 4 methylene, 9 methine, and 6 quaternary carbons; and (h) $^1H$ NMR spectrum displaying characteristics of a typical depsipeptide, illustrating three-amino protons [4.63, 4.31, 3.93], and one ester carbinol proton [5.69] and are described in US US20110207604 A1.

In a particular embodiment, the compound has the structure #STR001##:

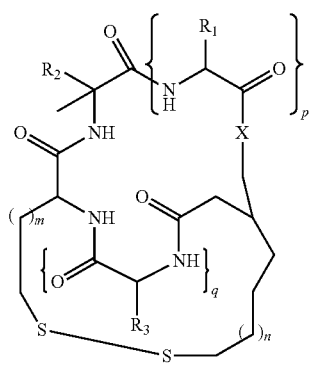

Or a pesticidally acceptable salt or stereoisomers thereof, wherein M is 1, 2, 3 or 4; n is 0, 1, 2, or 3; p and q are independently 1 or 2; X is O, NH or NR; R1, R2 and R3 are the same or different and independently an amino acid side-chain moiety or an amino acid side-chain derivative and R is a lower chain alkyl, aryl or arylalkyl moiety.

In an even more particular embodiment, the compound has the structure of FR901228:

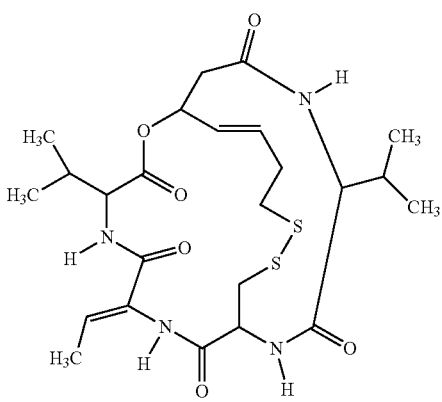 [SMILES: C/C=C1\NC(=O)C2CSSCC/C=C/C(CC(=O)NC(C(C)C)C(=O)N2)OC(=O)C(C(C)C)NC1=O]

Provided herewith are compounds set forth in ##STR002##:

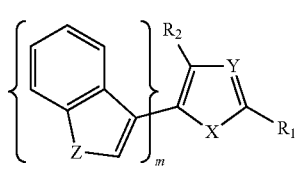

wherein: X, Y and Z are each independently —O, —NR$_1$, or —S, wherein R$_1$ is —H or C$_1$-C$_{10}$ alkyl; R$_1$, R$_2$ and m are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl.

These are from either natural materials or compounds obtained from commercial sources or by chemical synthesis. Natural sources of Family ##STR002## compounds include, but are not limited to, microorganisms, alga, and sponges. In a more particular embodiment, Family ##STR002## compounds may alternatively be derived from microorganism species including but not limited to, *Streptoverticillium waksmanii* (compound iv) (Umehara, et al., 1984), *Streptomyces pimprina* (compound v) (Naik et al., 2001), *Streptoverticillium olivoreticuli* (compounds vi, vii, viii) (Koyama Y., et al., 1981), *Streptomyces* sp (compounds ix, x) (Watabe et al., 1988), *Pseudomonas syringae* (compounds xi, xii) (Pettit et al., 2002). Family ##STR002## compounds may also be derived from algae including but not limited to red alga (compound xiii) (N'Diaye, et al., 1996), red alga *Martensia fragilis* (compound xiv) (Takahashi S. et al., 1998), *Diazona chinensis* (compounds xv & xvi) (Lindquist N. et al., 1991) and *Rhodophycota haraldiophyllum* sp (compound xvii) (Guella et al., 1994). In a particular embodiment, the substance is templazole A.

Also provided is ##STR003##:

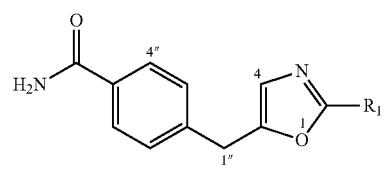

wherein: X and Y are each independently —OH, —NR$_1$, or —S, wherein R$_1$ is —H or C$_1$-C$_{10}$, alkyl; R$_1$, R$_2$ and m, a substituent on the oxazole ring, are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl. In a particular embodiment, the substance is templazole B.

Compositions

A substantially pure culture, cell fraction or supernatant and compounds which modulate glutamine derived from an inactivated *Burkholderia* strain disclosed herein, all of which are alternatively referred to as "active ingredient(s)", may be formulated into a composition, particularly a pesticidal and more particularly an herbicidal composition. In a particular embodiment, the supernatant may be a cell-free supernatant.

The active ingredient(s) set forth above can be formulated in any manner. Non-limiting formulation examples include but are not limited to emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), dusts, emulsions, liquids, flakes etc. In any formulation described herein, percent of the active ingredient is within a range of 0.01% to 99.99%.

A solid composition can be prepared by suspending a solid carrier in a solution of pesticidal compounds and drying the suspension under mild conditions, such as evaporation at room temperature or vacuum evaporation at 65° C. or lower. Alternatively, a solid composition may be derived via spray-drying or freeze-drying.

When referring to solid compositions, it should be understood by the artisan of ordinary skill that physical forms such as dusts, beads, powders, particulates, pellets, tablets, agglomerates, granules, floating solids and other known solid formulations are included. The artisan of ordinary skill will be able to readily optimize a particular solid formulation for a given application using methods well known to those of ordinary skill in the art.

The composition may comprise gel-encapsulated compounds derived from the Burkholderia strain set forth above. Such gel-encapsulated materials can be prepared by mixing a gel-forming agent (e.g., gelatin, cellulose, or lignin) with a solution of algicidal compounds and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic, non-ionic surfactant which preferably belongs to EPA List 4B. In another particular embodiment, the nonionic surfactant is polyoxyethylene (20) monolaurate. The concentration of surfactants may range between 0.1-35% of the total formulation, the preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of these compositions.

In order to provide compositions containing the active ingredient(s) set forth above in the form of dusts, granules, water dispersible powders, aqueous dispersions, or emulsions and dispersions in organic liquids, the carrier or diluent agent in such compositions may be a finely divided solid, an organic liquid, water, a wetting agent, a dispersing agent, humidifying agent, or emulsifying agent, or any suitable combination of these. Generally, when liquids and wettable powders are prepared, a conditioning agent comprising one or more surface-active agents or surfactants is present in amounts sufficient to render a given composition containing the active material, the microorganism, dispersible in water or oil.

Since these compositions can be applied as a spray utilizing a liquid carrier, it is contemplated that a wide variety of liquid carriers such as, for example, water, organic solvents, decane, dodecane, oils, vegetable oil, mineral oil, alcohol, glycol, polyethylene glycol, agents that result in a differential distribution of pathogenic bacterium in water being treated. combinations thereof and other known to artisan of ordinary skill can be used.

The present compositions can also include other substances which are not detrimental to the active ingredient(s) such as adjuvants, surfactants, binders, stabilizers and the like, which are commonly used in algicides, either singly or in combination as needed.

It will be understood by the artisan of ordinary skill that various additives or agents that predispose pests susceptible to the active ingredient set forth above are added to enhance its pesticidal action. By the phrase "additive that enhances the pesticidal action of the active ingredient" is meant any compound, solvent, reagent, substance, or agent that increases the effect of the active ingredient toward pests and more particularly, mites as compared to the pesticidal effect of the active ingredient in the absence of said additive. In some embodiments, these additives will increase the susceptibility of a particular pest to the active ingredient. Additional additives include but are not limited to agents which weaken the biological defenses of susceptible pests. Such agents can include salts, such as NaCl and $CaCl_2$.

The composition may further comprise another microorganism and/or herbicide. The microorganism may include but is not limited to an agent derived from *Bacillus* sp. (e.g., *Bacillus firmus, Bacillus thuringiensis, Bacillus pumilus, Bacillus licheniformis, Bacillus amyloliquefaciens, Bacillus subtilis*), *Paecilomyces* sp. (*P. lilacinus*), *Pasteuria* sp. (*P. penetrans*), *Chromobacterium* sp., *Pseudomonas* sp., *Brevabacillus* sp., *Lecanicillium* sp., *Ampelomyces* sp., *Pseudozyma* sp., *Streptomyces* sp (*S. bikiniensis, S. costaricanus, S. avermitilis*), *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorosplrnium, Neobulgaria, Daldinia, Aspergillus, Chaetomium, Lysobacter* spp, *Lachnum papyraceum, Verticillium suchlasporium, Arthrobotrys oligospora, Verticillium chlamydosporium, Hirsutella rhossiliensis, Pochonia chlamydosporia, Pleurotus ostreatus, Omphalotus olearius, Lampteromyces japonicas, Brevudimonas* sp., *Muscodor* sp., *Phoma* sp (e.g. *Phoma macrostoma*), *Mycoleptodiscus* sp.,

*Bacillus* sp., *Pseudomonas* sp., *Brevabacillus* sp., *Lecanicillium* sp., non-*Ampelomyces* sp., *Pseudozyma* sp., *Streptomyces* sp, *Burkholderia* sp, *Trichoderma* sp, *Gliocladium* sp. Alternatively, the agent may be a natural oil or oil-product having fungicidal, herbicidal, aracidal, algicidal, nematocidal and/or insecticidal activity (e.g., citrus oil including but not limited to bitter orange, orange, lemon; rosemary oil, allspice, bergamot, blue gum, chamomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, saponins paraffinic oil, tea tree oil, lemongrass oil, clove oil, cinnamon oil, citrus oil, rosemary oil).

As noted above, the compositions may be herbicidal compositions. The composition may further comprise one or more herbicides. These may include, but are not limited to, a bioherbicide and/or a chemical herbicide. The bioherbicide may be selected from the group consisting of clove oil, cinnamon oil, lemongrass oil, citrus oil, orange peel oil, tentoxin, cornexistin, AAL-toxin, manuka oil, leptospermone, thaxtomin, sarmentine, momilactone B, sorgoleone, ascaulatoxin and ascaulatoxin aglycone, corn gluten meal, pine oil, garlic oil, neem oil, karanja oil, pelargonic acid, vinegar, eugenol, citric acid, citronellal, geraniol, citral, limonene, 1-menthone, 1-menthol, 2-phenethyl propionate, p-cymene, γ-terpinene, thymol, m-tyrosene, phosphinothricin, tabtoxine-β-lactam, oxetin, phosalacin, methionine sulfoximine, benzoxazinoids; the bioherbicide may be selected from fungal pathogens such as *Phoma macrostoma, Alternaria, Fusarium, Colletotrichum*. macrocidins, hydantocidin. The chemical herbicide may include, but is not limited to, Acetochlor, Amicarbazone, Anilofos, Chlorthiamid, Cyhalofop-butyl, Dithiopyr, Diuron, EPTC, Flumioxazin, Fluiridone, Fluoroxypyr, Fomesafen, Indazifain, Isoxaben, Linuron, MCPA 4-chloro-2-methylphenoxy acetic acid), MCPP, MSMA, Napropamide, Norflurazon, Oleic acid, Oryzalin, Oxadiazon, Pelargonic acid, Picloram, Pyrithrobac-sodium, Saflufenacil, Sethoxydim, Simazine, Sulcotrione, Thiazopyr, Thiencarbazone, Trifluralin, Trioxysulfuron-sodium, diflufenzopyr and salts thereof, dicamba and salts thereof, topramezone, tembotrione, S-metolachlor, atrazine, mesotrione, primisulfuron-methyl, 2,4-dichlorophenoxyacetic acid, nicosulfuron, thifensulfuron-methyl, asulam, metribuzin, diclofop-methyl, fluazifop, fenoxaprop-p-ethyl, asulam, oxyfluorfen, rimsulfuron, mecoprop, and quinclorac, thiobencarb, clomazone, cyhalofop, propanil, bensulfuron-methyl, penoxsulam, triclopyr, imazethapyr, halosulfuron-methyl, pendimethalin, bispyribac-sodium, carfentrazone ethyl, sodium bentazon/sodium acifluorfen, glyphosate, glufosinate and orthosulfamuron.

Herbicidal compositions may be applied in liquid or solid form as pre-emergence or post-emergence formulations.

For pre-emergence dry formulations, the granule size of the carrier is typically 1-2 mm (diameter) but the granules can be either smaller or larger depending on the required ground coverage. Granules may comprise porous or non-porous particles.

For post-emergence formulations, the formulation components used may contain inorganic salts such potassium sorbate or ammonium nitrate, solvents such as propylene glycol, spreading agents, water conditioners, pH stabilizers, plant uptake enhancing agents like d-limonene or acetic acid, smectite clays, attapulgite clays and similar swelling clays, thickeners such as xanthan gums, gum Arabic and other polysaccharide thickeners as well as dispersion stabilizers such as nonionic surfactants (for example polyoxyethylene (20) monolaurate).

Identification of Glutamine Synthetase Modulators

As set forth above, potential glutamine synthetase activity modulators and particularly inhibitors may be identified by:
(a) contacting a plant glutamine synthetase with a test plant glutamine synthetase modulator and
(b) determining whether or not the activity of the glutamine synthetase is modulated relative to the activity of the glutamine synthetase that has not been contacted with the test glutamine synthetase modulator. The glutamine modulator may be a glutamine synthetase inhibitor and may inhibit glutamine synthetase activity at least about 30% and more particularly at least about 40% and even more particularly, at least about 50%.

The plant glutamine synthetase may be a cytosolic or plastidic glutamine synthetase. The glutamine synthetase may be directly isolated from the plant or may be obtained in recombinant form using methods known in the art.

The method may further comprise comparing the activity of the glutamine synthetase when contacted with a test plant glutamine synthetase modulator with the activity of the glutamine synthetase when contacted with a known plant glutamine synthetase modulator. This known substance may be a positive or negative control.

Further provided is a method for identifying a herbicidal substance comprising
(a) identifying a substance that inhibits plant glutamine synthetase activity according to the method set forth above and
(b) determining if said substance identified as a glutamine synthetase inhibitor in (a) has herbicidal activity.

Uses

The substances and compositions may also be used to modulate emergence in either a pre-emergent or post-emergent formulation of monocotyledonous, including sedges and grasses, or dicotyledonous weeds. In a particular embodiment, the weeds may include, but not be limited to, *Chenopodium* sp. (e.g., *Chenopodium album, Chenopodium murale*), *Abutilon* sp. (e.g., *Abutilon theophrasti*), *Helianthus* sp. (e.g., *Helianthus annuus*), *Ambrosia* sp. (e.g., *Ambrosia artemesifolia, Ambrosia trifida*), *Amaranthus* sp. (e.g., *Amaranthus retroflexus, Amaranthus palmeri, Amaranthus rudis, Amaranthus spinosus, Amaranthus tuberculatus*), *Convolvulus* sp. (e.g., *Convolvulus arvensis*), *Brassica* sp. (e.g., *Brassica kaber*), *Taraxacum* sp. (e.g., *Taraxacum officinale*), *Solanum* sp. (e.g., *Solanum nigrum, Solanum elaeagnifolium, Solanum physalifolium, Solanum ptycanthum*), *Malva* sp. (e.g., *Malva neglecta, Malva parviflora*), *Setaria* sp. (e.g., *Setaria lutescens*), *Bromus* sp. (e.g., *Bromus tectorum, Bromus diandrus, Bromus hordeaceus*), *Poa* sp. (e.g., *Poa annua, Poa pratensis*), *Lolium* sp. (e.g., *Lolium perenne, Lolium rigidum, Lolium multiflorum* L. var. Pace), *Festuca* sp. (e.g., *Festuca arundinaceae, Festuca rubra*), *Echinochloa* sp. (e.g., *Echinochloa crus-galli, Echinochloa colona*), *Oxalis* sp. (e.g., *Oxalis stricta, Oxalis pes-caprae, Oxalis corniculata*); *Cyperus* sp. (e.g., *Cyperus difformis, Cyperus esculentum, Cyperus rotundus, Cyperus brevifolius*); *Conyza* sp. (e.g., *Conyza canadensis, Conyza sumatrensis, Conyza bonariensis*); *Sagina* sp. (e.g., *Sagina procumbens*); *Pueraria lobata, Veronica* sp. (e.g., *Veronica hederafolia*), *Stellaria* sp. (e.g., *Stellaria media*), *Rorippa* sp. (e.g., *Rorippa islandica*), *Senecio* sp. (e.g., *Senecio vulgaris*), *Lamium* sp. (e.g., *Lamium amplexicaule*), *Digitaria* sp. (e.g., *Digitaria sanguinalis, Digitaria ischaemum*), *Trifolium* sp. (e.g., *Trifolium repens, Trifolium hirtum, Trifolium incarnatum, Trifolium pratense*), *Alhagi maurorum, Astragalus* spp., *Medicago* sp. (e.g. *Medicago lupulina, Medicago polymorpha*), *Melilotus* sp., *Sesbania* sp. (e.g. *Sesbania punicea, Sesbania exaltata*), *Vicia* sp. (e.g. *Vicia sativa, Vicia villosa*), *Gallium* sp. (e.g., *Gallium aparine*), *Galinsoga* sp. (e.g., *Galinsoga aristatula*), *Cardamine* sp. (e.g., *Cardamine flexuosa, Cardamine hirsuta*), *Kochia* sp. (e.g., *Kochia scoparia*), *Eleusine* sp. (e.g., *Eleusine indica*), *Portulaca* sp. (e.g., *Portulaca oleraceae*), *Plantago* sp. (e.g., *Plantago lanceolata*), *Euphorbia* sp. (e.g., *Euphornia supina, Euphorbia maculate, Euphorbia esula, Euphorbia prostrata*), *Erodium* sp. (e.g., *Erodium cicutarium*), *Sonchus* sp., (e.g., *Sonchus oleraceus*), *Lactuca* sp. (e.g., *Lactuca serriola*), *Capsella* sp. (e.g., *Capsella bursa-pastoris*), *Leptochloa* sp. (e.g., *Leptochloa fascicularis, Leptochloa virgata*), *Raphanus* sp. (e.g., *Raphanus raphanistrum*), *Calandrinia* sp. (e.g., *Calandrinia ciliata*), *Paspalum* sp. (e.g., *Paspalum dilatatum*), *Gnaphalium* sp., *Cynodon* sp. (e.g., *Cynodon dactylon, Cynodon hirsutus*), *Polygonum* sp. (e.g., *Polygonum arenastrum, Polygonum lapathifolium,*), *Avena fatua, Hordeum* sp. (e.g., *Hordeum leporinum*), *Urtica* sp. (e.g., *Urtica urens*), *Tribulus terrestris, Sisymbrium* sp. (e.g., *Sisymbrium irio*), *Cenchrus* sp., *Salsola* sp. (e.g., *Salsola tragus, Salsola kali*), *Amsinckia* sp. (e.g., *Amsinckia lycopsoides*), *Ipomoea* sp., *Claytonia perfoliata, Polypogon* sp. (e.g., *Polypogon monspeliensis*), *Xanthium* sp., *Hypochaeris radicata, Physalis* sp., *Eragrostis* sp., *Verbascum* sp.,

*Chamomilla suaveolens, Centaurea* sp. (e.g., *Centaurea solstitialis*), *Epilobium brachycarpum, Panicum* sp. (e.g., *Panicum capilare, Panicum dichotomiflorum*), *Rumex acetosella, Eclipta* sp. (e.g., *Eclipta alba, Eclipta prostrata*), *Ludwigia* sp., *Urochloa* sp. (e.g. *Urochloa platyphylla, Urochloa panicoides*), *Leersia* sp., *Sesbania* sp. (*Sesbania herbacea*), *Lotus major, Rotala* sp., *Ammania* sp., *Alternathera philoxeroides, Commelina* sp., *Sorghum halepense, Parthenium hysterophorus, Chloris truncata*, and species in the Fabaceae family. In a particular embodiment, the weed is *Ambrosia artemisifolia, Solanum nigrum Convolvulus arvensis.*

EXAMPLES

The compositions and methods set forth above will be further illustrated in the following, non-limiting examples. The examples are illustrative of various embodiments only and do not limit the claimed invention regarding the materials, conditions, weight ratios, process parameters and the like recited herein.

Example 1

Isolation and Identification of the Microbe

Isolation of the Microorganism

The microbe is isolated using established techniques known to the art from a soil sample collected under an evergreen tree at the Rinnoji Temple, Nikko, Japan. The isolation is done using potato dextrose agar (PDA) using a procedure described in detail by Lorch et al., 1995. In this procedure, the soil sample is first diluted in sterile water, after which it is plated in a solid agar medium such as potato dextrose agar (PDA). The plates are grown at 25° C. for five days, after which individual microbial colonies are isolated into separate PDA plates. The isolated bacterium is gram negative, and it forms round, opaque cream-colored colonies that change to pink and pinkish-brown in color and mucoid or slimy over time.

Identification of the Microorganism

The microbe is identified based on gene sequencing using universal bacterial primers to amplify the 16s rRNA region. The following protocol is used: *Burkholderia* sp A396 is cultured on potato-dextrose agar plates. Growth from a 24 hour-old plate is scraped with a sterile loop and re-suspended in DNA extraction buffer. DNA is extracted using the MoBio Ultra Clean Microbial DNA extraction kit. DNA extract is checked for quality/quantity by running 5 µl on a 1% agarose gel.

PCR reactions are set up as follows: 2 µl DNA extract, 5 µl PCR buffer, 1 µl dNTPs (10 mM each), 1.25 µl forward primer (27F; 5'-AGAGTTTGATCCTGGCTCAG-3' (SEQ ID NO:1), 1.25 µl reverse primer (907R; 5'-CCGTCAATTC-CTTTGAGTTT-3' (SEQ ID NO:2)) and 0.25 µl Taq enzyme. The reaction volume is made up to 50 µl using sterile nuclease-free water. The PCR reaction includes an initial denaturation step at 95° C. for 10 minutes, followed by 30 cycles of 94° C./30 sec, 57° C./20 sec, 72° C./30 sec, and a final extension step at 72° C. for 10 minutes.

The product's approximate concentration and size is calculated by running a 5 µl volume on a 1% agarose gel and comparing the product band to a mass ladder.

Excess primers, dNTPs and enzyme are removed from the PCR product with the MoBio PCR clean up kit. The cleaned PCR product as directly sequenced using primers 27F (same as above), 530F (5'-GTGCCAGCCGCCGCGG-3' (SEQ ID NO:3)), 1114F (5'-GCAACGAGCGCAACCC (SEQ ID NO:4)) and 1525R (5'-AAGGAGGTGWTCCARCC-3' (SEQ ID NO:5)), 1100R (5'-GGGTTGCGCTCGTTG-3' (SEQ ID NO:6)), 519R (5'-GWATTACCGCGGCKGCTG-3' (SEQ ID NO:7)).

The 16s rRNA gene sequence of strain A396 is compared with the available 16s rRNA gene sequences of representatives of the β-proteobacteria using BLAST. Strain A395 A396 is closely related to members of the *Burkholderia cepacia* complex, with 99% or higher similarity to several isolates of *Burkholderia multivorans, Burkholderia vietnamensis*, and *Burkholderia cepacia*. A BLAST search excluding the *B. cepacia* complex, showed 98% similarity to *B. plantarii, B. gladioli* and *Burkholderia* sp. isolates.

A distance tree of results using the neighbor joining method, showed that A396 is related to *Burkholderia multivorans* and other *Burkholderia cepacia* complex isolates. *Burkholderia plantarii* and *Burkholderia glumae* are grouped in a separate branch of the tree.

The isolated *Burkholderia* strain was found to contain the following sequences:

Forward sequence, DNA sequence with 27F primer, 815 nucleotides (SEQ ID NO: 8)
TGCAGTCGAACGGCAGCACGGGTGCTTGCACCTGGTGGCGAGTGGCGAAC

GGGTGAGTAATACATCGGAACATGTCCTGTAGTGGGGGATAGCCCGGCGA

AAGCCGGATTAATACCGCATACGATCTACGGATGAAAGCGGGGGATCTTC

GGACCTCGCGCTATAGGGTTGGCCGATGGCTGATTAGCTAGTTGGTGGGG

TAAAGGCCTACCAAGGCGACGATCAGTAGCTGGTCTGAGAGGACGATCAG

CCACACTGGGACTGAGACACGGCCCAGACTCCTACGGGAGGCAGCAGTGG

GGAATTTTGGACAATGGGGGAAACCCTGATCCAGCAATGCCGCGTGTGTG

AAGAAGGCCTTCGGGTTGTAAAGCACTTTTGTCCGGAAAGAAATCCTTTG

GGCTAATACCCCGGGGGATGACGGTACCGGAAGAATAAGCACCGGCTAA

CTACGTGCCAGCAGCCGCGGTAATACGTAGGGTGCGAGCGTTAATCGGAA

TTACTGGGCGTAAAGCGTGCGCAGGCGGTTTGTTAAGACAGATGTGAAAT

CCCCGGGCTTAACCTGGGAACTGCATTTGTGACTGGCAAGCTAGAGTATG

GCAGAGGGGGGTAGAATTCCACGTGTAGCAGTGAAATGCGTAGAGATGTG

GAGGAATACCGATGGCGAAGGCAGCCCCCTGGGCCAATACTGACGCTCAT

GCACGAAAGCGTGGGGAGCAAACAGGATTAGATACCCTGGTAGTCCACGC

CCTAAACGATGTCAACTAGTTGTTGGGGATTCATTTCCTTAGTAACGTAG

CTACGCGTGAAGTTGACCGCCTGGGGAGTACGGTCGCAAGATTAAATMGA

GGGTKGKKTGKKGGGGGGAAA

Reverse sequence, 1453 bp, using primers 1525R, 1100R, 519R (SEQ ID NO: 9)
GTCATGAATCCTACCGTGGTGACCGTCCTCCTTGCGGTTAGACTAGCCAC

TTCTGGTAAAACCCACTCCCATGGTGTGACGGGCGGTGTGTACAAGACCC

GGGAACGTATTCACCGCGGCATGCTGATCCGCGATTACTAGCGATTCCAG

CTTCATGCACTCGAGTTGCAGAGTGCAATCCGGACTACGATCGGTTTTCT

GGGATTAGCTCCCCCTCGCGGGTTGGCAACCCTCTGTTCCGACCATTGTA

TGACGTGTGAAGCCCTACCCATAAGGGCCATGAGGACTTGACGTCATCCC

CACCTTCCTCCGGTTTGTCACCGGCAGTCTCCTTAGAGTGCTCTTGCGTA

-continued

GCAACTAAGGACAAGGGTTGCGCTCGTTGCGGGACTTAACCCAACATCTC

ACGACACGAGCTGACGACAGCCATGCAGCACCTGTGTATCGGTTCTCTTT

CGAGCACTCCCGAATCTCTTCAGGATTCCGACCATGTCAAGGGTAGGTAA

GGTTTTTCGCGTTGCATCGAATTAATCCACATCATCCACCGCTTGTGCGG

GTCCCCGTCAATTCCTTTGAGTTTTAATCTTGCGACCGTACTCCCCAGGC

GGTCAACTTCACGCGTTAGCTACGTTACTAAGGAAATGAATCCCCAACAA

CTAGTTGACATCGTTTAGGGCGTGGACTACCAGGGTATCTAATCCTGTTT

GCTCCCCACGCTTTCGTGCATGAGCGTCAGTATTGGCCCAGGGGGCTGCC

TTCGCCATCGGTATTCCTCCACATCTCTACGCATTTCACTGCTACACGTG

GAATTCTACCCCCCTCTGCCATACTCTAGCTTGCCAGTCACAAATGCAGT

TCCCAGGTTAAGCCCGGGGATTTCACATCTGTCTTAACAAACCGCCTGCG

CACGCTTTACGCCCAGTAATTCCGATTAACGCTCGCACCCTACGTATTAC

CGCGGCTGCTGGCACGTAGTTAGCCGGTGCTTATTCTTCCGGTACCGTCA

TCCCCCCGGGGTATTAGCCCAAAGGATTTCTTTCCGGACAAAAGTGCTTT

ACAACCCGAAGGCCTTCTTCACACACGCGGCATTGCTGGATCAGGGTTTC

CCCCATTGTCCAAAATTCCCCACTGCTGCCTCCCGTAGGAGTCTGGGCCG

TGTCTCAGTCCCAGTGTGGCTGATCGTCCTCTCAGACCAGCTACTGATCG

TCGCCTTGGTAGGCCTTTACCCCACCAACTAGCTAATCAGCCATCGGCCA

ACCCTATAGCGCGAGGTCCGAAGATCCCCGCTTTCATCCGTAGATCGTA

TGCGGTATTAATCCGGCTTTCGCCGGGCTATCCCCCACTACAGGACATGT

TCCGATGTATTACTCACCCGTTCGCCACTCGCCACCAGGTGCAAGCACCC

GTGCTGCCGTTCGACTTGCATGTGTAAGGCATGCCGCCAGCGTTCAATCT

GAG.

Reverse sequence 824 bp using primer 907R (SEQ NO: 10)

CCAGGCGGTCACTTCACGCGTTAGCTACGTTACTAAGGAAATGAATCCCC

AACAACTAGTTGACATCGTTTAGGGCGTGGACTACCAGGGTATCTAATCC

TGTTTGCTCCCCACGCTTTCGTGCATGAGCGTCAGTATTGGCCCAGGGGG

CTGCCTTCGCCATCGGTATTCCTCCACATCTCTACGCATTTCACTGCTAC

ACGTGGAATTCTACCCCCCTCTGCCATACTCTAGCTTGCCAGTCACAAAT

GCAGTTCCCAGGTTAAGCCCGGGGATTTCACATCTGTCTTAACAAACCGC

CTGCGCACGCTTTACGCCCAGTAATTCCGATTAACGCTCGCACCCTACGT

ATTACCGCGGCTGCTGGCACGTAGTTAGCCGGTGCTTATTCTTCCGGTAC

CGTCATCCCCCCGGGGTATTAGCCCAAAGGATTTCTTTCCGGACAAAAGT

GCTTTACAACCCGAAGGCCTTCTTCACACACGCGGCATTGCTGGATCAGG

GTTTCCCCCATTGTCCAAAATTCCCCACTGCTGCCTCCCGTAGGAGTCTG

GGCCGTGTCTCAGTCCCAGTGTGGCTGATCGTCCTCTCAGACCAGCTACT

GATCGTCGCCTTGGTAGGCCTTTACCCCACCAACTAGCTAATCAGCCATC

GGCCAACCCTATAGCGCGAGGTCCGAAGATCCCCGCTTTCATCCGTAGA

TCGTATGCGGTATTAATCCGGCTTTCGCCGGGCTATCCCCCACTACAGGA

CATGTTCCGATGTATTACTCACCCGTTCGCCACTCGCCACCAGGTGCAAG

CACCCGTGCTGCCGTTCGACTTGCATGTGTAAGGCATGCCGCCAGCGTTC

AATCTGAGTG

Forward sequence 1152 bp using primer 530F (SEQ ID NO: 11)

TCGGATTACTGGGCGTAAGCGTGCGCAGGCGGTTTGTTAAGACAGATGTG

AAATCCCCGGGCTTAACCTGGGAACTGCATTTGTGACTGGCAAGCTAGAG

TATGGCAGAGGGGGTAGAATTCCACGTGTAGCAGTGAAATGCGTAGAGA

TGTGGAGGAATACCGATGGCGAAGGGAGCCCCCTGGGCCTATACTGACCC

TCATGCTCGAAAGCGTGAGGACCCAACCGGATTAGATGCCCTGATAGGCC

ATGCCCCACACCATGCCATGTGTTAGGGGCCCATTTCCTTAGGGAGGCAG

CTATGGGAATTTTGGACAATGTGGGAAACCCTGATCCAACAATGCCGCG

TGTGTGAATAAGGCCTTCGGGTTGTAAAGCACTTTTATCCGGATAGATTC

CTTTTGGGCTAAACCTCCGTAGGGGATGACGGTACCGGAAGAATAACCAC

CGGGTAACTACGTGCCAGCAGCCGCGGTAATACGTAGGGTGCGAGCGTTA

ATCGGAATTACTGGGCGTAAAGCGTGCGCAGGCGGTTTGTTAAGACAGAT

GTGAAATCCCCGGGCTTAACCTGGGAACTGCATTTGTGACTGGCAAGCTA

GAGTATGGCAGACGGGGTAGAATTCCACGTGTAGCAGTGAAATGCGTAG

AGATGTGGAGGAATACCGATGGGCGAAGCAGCTCCTGGGCAATACTGAC

GCTCATGCACAAGATCGTGCGAAACAAACAGGATAAAACCCCTGTATTCC

ACGCCCAAAACGATGTCCACCAAGTTGTTGGCGATCCTTTCCTTCGTATC

GTAGCTACGCGGGAATTTGACCCCCTGGGGACTAGGCCGCATATAAAACT

CAAGGGAATTCCGGGACCCCCAGAGCTGTGTATGATGTGATTATTCCGA

TGCGCGGAAAACCTTCCTTATCTTTGAATGGCGGTACTCCTGAAAATTGC

GGAGTGCTCGAAAACACCGAACCCGGGTCTTTCTGCGTGTCCTCCCTCGT

GTGGGATATGCTGGATATCCCGCAGACGCATCTTTGACTTAGTGCTCCCA

AAACTGAGAGCTGGGAGGACTCGAGAGGGGATCCCTGCCTCCCCGGCTTG

GGTGCTCCCCTTATGGGGGAAACAGGTACACGGGGGGATCATCCCATACC

TA

Forward sequence 1067 bp using 1114F primer (SEQ ID NO: 12)

TCTAAGGAGACTGCCGGTGACAAACCGGAGGAAGGTGGGGATGACGTCAA

GTCCTCATGGCCCTTATGGGTAGGGCTTCACACGTCATACAATGGTCGGA

ACAGAGGGTTGCCAACCCGCGAGGGGAGCTAATCCCAGAAAACCGATCG

TAGTCCGGATTGCACTCTGCAACTCGAGTGCATGAAGCTGGAATCGCTAG

TAATCGCGGATCAGCATGCCGCGGTGAATACGTTCCCGGGTCTTGTACAC

ACCGCCCGTCACACCATGGGAGTGGGTTTTACCAGAAGTGGCTAGTCTAA

CCGCAAGGAGGACGGTCACCACGGTAGGATTCATGACTGGGGTGAAGTCG

TAACAAGGTAGCCGTATCGGAAGGTGCGGCTGGATCACCTCCTTAAACCC

TTTGGCCTAATAACCCGGGGGAATAAGTACCGAAAAAAAAAAAAACTGG

ATAACTTCCGTGCCACAACCCGCGGAAAAATCTAGGGGGGGGAGCTTAA

ATGGAAATTTACGGGCCGTAAAGCGTGCGCAGGCGGTTTGTAAACACAG

ATGTGAAATCCCCGGGCTTAACCTGGGAACTGCATTTGTGACTGGCAAGC

TAGAGTATGGCACAGGGGGGTAGAATTCCACGTGTAGCATTGAATGCATA

GAGATGAGAGGATACCGATGGAGAAGGGCGCCCCGGGGACAATATGACG

CCTATGCCACAAAGCTGTGGCACAATAGGTTAAATACCTGTGTTGTCCCC

GCCTAAACAGATTACACTTGTTGTGGGTATTTTCTCATAAAATACTACAC

ACGGGAGAATACACTGGGGGGCTTCGTCAATTATCACAACAATGATTGCG

GGCACCCACGGGGGTAGATGGGTAATAAATCGACGGCAACTATCTACTTA

CTTGGATGATCGCACAGATTGGGCGGGAGAGAAGAGAACAGCGTGTGTGT

GCTCCTCCGCGAGTGATAGGTAATCGGACAATACTTTGACAGGACTTAAC

TGGGTAGCGGGATCGAGTGGATTCCCGTCGGATGGCCTCCGCAGGTACGG

CAGCTGGGGATTACATC

Reverse sequence 1223 bp using 1525R primer
(SEQ NO: 13)
TTGCTTACGACTTCACCCCAGTCATGAATCCTACCGTGGTGACCGTCCTC

CTTGCGGTTAGACTAGCCACTTCTGGTAAAACCCACTCCCATGGTGTGAC

GGGCGGTGTGTACAAGACCCGGGAACGTATTCACCGCGGCATGCTGATCC

GCGATTACTAGCGATTCCAGCTTCATGCACTCGAGTTGCAGAGTGCAATC

CGGACTACGATCGGTTTTCTGGGATTAGCTCCCCCTCGCGGGTTGGCAAC

CCTCTGTTCCGACCATTGTATGACGTGTGAAGCCCTACCCATAAGGGCCA

TGAGGACTTGACGTCATCCCCACCTTCCTCCGGTTTGTCACCGGCAGTCT

CCTTAGAGTGCTCTTGCGTAGCAACTAAGGACAAGGGTTGCGCTCGTTGC

GGGACTTAACCCAACATCTCACGACACGAGCTGACGACAGCCATGCAGCA

CCTGTGTATCGGTTCTCTTTCGAGCACTCCCGAATCTCTTCAGGATTCCG

ACCATGTCAAGGGTAGGTAAGGTTTTTCGCGTTGCATCGAATTAATCCAC

ATCATCCACCGCTTGTGCGGGTCCCCGTCAATTCCTTTGAGTTTTAATCT

TGCGACCGTACTCCCCAGGCGGTCAACTTCACGCGTTAGCTACGTTACTA

AGGAAATGAATCCCCAACAACTAGTTGACATCGTTTAGGGCGTGGACTAC

CAGGGTATCTAATCCTGTTTGCTCCCCACGCTTTCGTGCATGAGCGTCAG

TATTGGCCCAGGGGGCTGCCTTCGCCATCGGTATTCCTCCACATCTCTAC

GCATTTCACTGCTACACGTGGAATTCTACCCCCCTCTGCCATACTCTAGC

TTGCCAGTCACAAATGCAGTTCCCAGGTTAAGCCCGGGGATTTCACATC+

TGTCTTAACAAACCGCCTGCGCACGCTTTACGCCCAGTAATTCCGATTAA

CGCTCGCACCCTACGTATTACCGCGGCTGCTGGCACGTAGTTAGCCGGTG

CTTATTCTGCGGTACCGTCATCCCCCGGGTATAGCCCAAAGGATTCTTTC

GACAAAGTGCTTTACACCCGATGTCTCTCACACACGCGCATGCTGATCAG

GTTTCCCCATGTCAAAGTCCACTGCTGCTCGTAGGTCTGACGGGTTCAG

TTCAATGTGACTGATCGTCTTTCGACAACTACTGAACGTCCCTGTAGCTT

ACCCACCAACTAGCTATAGCATGC

Reverse sequence 1216 bp using 1100R primer
(SEQ ID NO: 14)
CCGAGCTGACGACAGCCATGCAGCACCTGTGTATCGGTTCTCTTTCGAGC

ACTCCCGAATCTCTTCAGGATTCCGACCATGTCAAGGGTAGGTAAGGTTT

TTCGCGTTGCATCGAATTAATCCACATCATCCACCGCTTGTGCGGGTCCC

CGTCAATTCCTTTGAGTTTTAATCTTGCGACCGTACTCCCCAGGCGGTCA

ACTTCACGCGTTAGCTACGTTACTAAGGAAATGAATCCCCAACAACTAGT

TGACATCGTTTAGGGCGTGGACTACCAGGGTATCTAATCCTGTTTGCTCC

CCACGCTTTCGTGCATGAGCGTCAGTATTGGCCCAGGGGGCTGCCTTCGC

CATCGGTATTCCTCCACATCTCTACGCATTTCACTGCTACACGTGGAATT

CTACCCCCCTCTGCCATACTCTAGCTTGCCAGTCACAAATGCAGTTCCCA

GGTTAAGCCCGGGGATTTCACATCTGTCTTAACAAACCGCCTGCGCACGC

TTTACGCCCAGTAATTCCGATTAACGCTCGCACCCTACGTATTACCGCGG

CTGCTGGCACGTAGTTAGCCGGTGCTTATTCTTCCGGTACCGTCATCCCC

CCGGGGTATTAGCCCAAAGGATTTCTTTCCGGACAAAAGTGCTTTACAAC

CCGAAGGCCTTCTTCACACACGCGGCATTGCTGGATCAGGGTTTCCCCCA

TTGTCCAAAATTCCCCACTGCTGCCTCCCGTAGGAGTCTGGGCCGTGTCT

CAGTCCCAGTGTGGCTGATCGTCCTCTCAGACCAGCTACTGATCGTCGCC

TTGGTAGGCCTTTACCCCACCAACTAGCTAATCAGCCATCGGCCAACCCT

ATAGCGCGAGGTCCGAAGATCCCCCGCTTTCATCCGTAGATCGTATGCGG

TATTAATCCGGCTTTCGCCGGGCTATCCCCCACTACAGGACATGTTCCGA

TGTATTACTCACCCGTTCGCCACTCGCCCCAGGTGCAAGCACCCGTGCTG

CCGTTCGACTTGCATGTGTAGCATGCGCAGCGTCATCTACTAAATAAACA

ACTCTAAGAATTTTTGCCCGAGGGCCTCTAAACACTCGGGGCGTCGAGAG

AGACTACGGATGAGGAGCATCCCTCTGTCTCTAGGTATGTGTTGTCGCCT

CTCTCACAGAGGAGGGACGCACGACGGAGCCATCGGGGACGACAACATG

TACGATATACTATCTA

Reverse sequence 1194 bp using 519R primer
(SEQ ID NO: 15)
TTCTTCGGTACCGTCATCCCCCCGGGGTATTAGCCCAAAGGATTTCTTTC

CGGACAAAAGTGCTTTACAACCCGAAGGCCTTCTTCACACACGCGGCATT

GCTGGATCAGGGTTTCCCCCATTGTCCAAAATTCCCCACTGCTGCCTCCC

GTAGGAGTCTGGGCCGTGTCTCAGTCCCAGTGTGGCTGATCGTCCTCTCA

GACCAGCTACTGATCGTCGCCTTGGTAGGCCTTTACCCCACCAACTAGCT

AATCAGCCATCGGCCAACCCTATAGCGCGAGGTCCGAAGATCCCCCGCTT

TCATCCGTAGATCGTATGCGGTATTAATCCGGCTTTCGCCGGGCTATCCC

CCACTACAGGACATGTTCCGATGTATTACTCACCCGTTCGCCACTCGCCA

CCAGGTGCAAGCACCCGTGCTGCCGTTCGACTTGCATGTGTAAGGCATGC

CGCCAGCGTTCAATCTGAGCCATGATCAAACTCTGAGGGGGGGGCCTTC

AACGGAACGACTGGGCAAAAAGCGTGCCCAGGCGTTTTGTTAAGACAGAT

GTGAAACCCCGGGGCTTAACCTGGAAACTGCATTTGTGACTGGAAAGCTA

GAGTATGGCAGAGGGGGTAGAATTCCACGTGTAGCATTGAAATGCGTAG

AAATGGAGAGGAATACCGATGGGAGAGGGCAGCCCCCGTGGGCAAATACT

GGCGCTTATGAACAAAGTTGGGGCGCGCCGCCGGGATATGTTCCCCTGGG

ATATCCCCCCCTAAACTGCTTACAAATATTGTGTGGGAACTTTTTCTC

TAAAAAATAGAACACAACGGGAGATATCACCCCCGGGGGCCACCGCCAG

ATTAAACCCCCAAAAGTATTTGGCGGGCACCCCCCCGGGGGGTGAGATG

GGGTAAAATAAATCCGTGCGACGAGCAAACCCTCCCCACACCTGGGATGG

-continued

TCGCGACCACAGATGAGATGCGGGCGGAGAGAACGATACCCAAGCGTGGT

TGTTTGCCTGCATCCCCTCCGTCGGGAGTGGATATAGTAGAGTAATTACG

GCACGACTGCATTTTTTTTCTTCAGTACACCTTATCACACTGTTGGATG

CACCGCGAGAAATCCGGAGGTGTGAGTACTCCCCCCCTCTCCTCGGGATG

TGTCGGCGCTCCCTTCTCCCGTTCAGGGGTGGGTAAGCACCGCG

Proof that *Burkholderia* A396 does not Belong to *Burkholderia cepacia* Complex.

Molecular Biology Work Using Specific PCR Primers

In order to confirm the identification of *Burkholderia* A396 as *Burkholderia multivorans*, additional sequencing of housekeeping genes is performed. *Burkholderia multivorans* is a known member of the *Burkholderia cepacia* complex. Efforts are focused on PCR of recA genes, as described by Mahenthiralingam et al., 2000. The following primers are used: (a) BCR1 and BCR2 set forth in Mahenthiralingam et al., 2000 to confirm *B. cepacia* complex match and (b) BCRBM1 and BCRBM2 set forth Mahenthiralingam et al, 2000 to confirm *B. multivorans* match. A product-yielding PCR reaction for the first primer set would confirm that the microbe belongs to the *B. cepacia* complex. A product-yielding PCR reaction for the second primer set would confirm that the microbe is indeed *B. multivorans.*

No PCR product is obtained for either pair of primers. The performance of the PCR reaction and primers is tested using *Burkholderia multivorans* ATCC 17616 (positive control) and *Pseudomonas fluorescens* (negative control). Strong bands are observed both for *B. multivorans* using both sets of bvprimers. No bands are observed for *Pseudomonas fluorescens*. The results indicate that A396 is a *Burkholderia*, but not a member of the *B. cepacia* complex, and not *Burkholderia multivorans*. This is also demonstrated in a comparative culture experiment in which both A396 and a type culture of *B. multivorans* are grown side-by-side in a shake culture, and the growth is monitored daily using optical density measurements at 600 nm. Under the set conditions, the novel species A396 grew much faster than the *B. multivorans* type strain.

DNA-DNA Hybridization

In order to confirm that isolate A396 is a new species of *Burkholderia*, a DNA-DNA hybridization experiment with *Burkholderia multivorans* (the closest 16SrRNA sequence match) is conducted. Biomass for both A396 and *B. multivorans* is produced in ISP2 broth, grown over 48 hours at 200 rpm/25° C. in Fernbach flasks. The biomass is aseptically harvested by centrifugation. The broth is decanted and the cell pellet is resuspended in a 1:1 solution of water: isopropanol. DNA-DNA hybridization experiments are performed by the DSMZ, the German Collection of Microorganisms and Cell Cultures in Germany. DNA is isolated using a French pressure cell (Thermo Spectronic) and is purified by chromatography on hydroxyapatite as described by Cashion et al., 1977. DNA-DNA hybridization is carried out as described by De Ley et al., 1970 under consideration of the modifications described by Huss et al., 1983 using a model Cary 100 Bio UV/VIS-spectrophotometer equipped with a Peltier thermostatted 6×6 multicell changer and a temperature controller with in-situ temperature probe (Varian). DSMZ reported % DNA-DNA similarly between A396 and *Burkholderia multivorans* of 37.4%. The results indicate that *Burkholderia* sp strain A396 does not belong to the species *Burkholderia multivorans* when the recommendations of a threshold value of 70% DNA-DNA similarity for the definition of bacterial species by the ad hoc committee (Wayne et al., 1987) are considered.

Biochemical Profile Using Biolog GN2 Plates

For the carbon source utilization profile, A396 is grown overnight on Potato Dextrose Agar (PDA). The culture is transferred to BUG agar to produce an adequate culture for Biolog experiments as recommended by the manufacturer (Biolog, Hayward, Calif.).

The biochemical profile of the microorganism is determined by inoculating onto a Biolog GN2 plate and reading the plate after a 24-hour incubation using the MicroLog 4-automated microstation system. Identification of the unknown bacteria is attempted by comparing its carbon utilization pattern with the Microlog 4 Gram negative database.

No clear definitive matches are found to the Biolog profile. The closest matches all had less than 35% similarity with A396: *Pseudomonas spinosa* (*Burkholderia*), *Burkholderia cepacia*, and *Burkholderia pseudomallei*. The results are shown in Table I.

TABLE 1

Biochemical Profile of A396

| Substrate | Result | Substrate | Result |
|---|---|---|---|
| Cyclodextrin | − | L-arabinose | − |
| Dextrin | − | D-arabitol | − |
| Glycogen | − | D-cellobiose | − |
| Tween 40 | + | Erythritol | − |
| Tween 80 | + | D-Fructose | − |
| N-acetyl-D-Galactoseamine | − | L-Fucose | − |
| N-acetyl-D-glucosamine | − | D-Galactose | +/− |
| Adonitol | − | Gentibiose | − |
| Succinic Acid Mon-methyl ester | − | D-Glucose | + |
| Acetic acid | − | m-Inositol | − |
| Cis-aconitic acid | − | D-Lactose | − |
| Citric acid | − | Lactulose | − |
| Formic acid | + | Maltose | − |
| D-Galactonic Acid Lactone | − | D-Mannitol | − |
| D-Galacturonic Acid | − | D-Mannose | − |
| D-Gluconic acid | − | D-Melibiose | − |
| D-Glucosaminic acid | − | β-methyl-D-glucoside | − |
| D-Glucuronic Acid | − | D-Psicose | − |
| α-hydroxyburytic acid | − | D-Raffinose | − |
| β-hydroxybutyric acid | + | L-Rhamonose | − |
| γ-hydroxybutyric acid | − | D-Sorbitol | − |
| p-hydroxyphenylacetic acid | − | Sucrose | − |
| Itaconic acid | − | D-Trehalose | − |
| α-keto butyric acid | − | Turanose | − |
| α-keto glutaric acid | − | Xylitol | − |
| α-keto valeric acid | − | Pyruvic Acid Methyl esther | − |
| D,L-Lactic acid | − | Uridine | − |
| Malonic acid | − | Thymidine | − |
| Propionic acid | + | Phenyethyl-amine | − |
| Quinic acid | − | Putrescine | − |
| D-Saccharic acid | − | 2-aminoethanol | − |
| Sebacic acid | − | 2,3-Butanediol | − |
| Succinic Acid | + | Glycerol | +/− |
| Bromosuccinic acid | − | D,L-a-glycerol phosphate | +/− |
| Succinamic acid | − | α-D-Glucose-1-phosphate | − |
| Glucuronamide | − | D-glucose-6-phosphate | + |
| L-alaninamide | + | γ-amino butyric acid | + |
| D-Alanine | − | Urocanic acid | − |
| L-alanine | + | Inosine | − |
| L-alanyl-glycine | − | L-phenylalanine | + |
| L-asparagine | + | L-proline | − |
| L-aspartic acid | +/− | L-pyroglutamic acid | − |
| L-glutamic acid | + | D-serine | − |
| Glycyl-L-Aspartic acid | − | L-serine | − |
| Glycyl-L-glutamic acid | − | L-threonine | − |
| L-histidine | − | D,L-carnitine | − |

TABLE 1-continued

Biochemical Profile of A396

| Substrate | Result | Substrate | Result |
|---|---|---|---|
| Hydroxy-L-proline | + | L-ornithine | − |
| L-leucine | − | | |

Fatty Acid Composition

After incubation for 24 hours at 28° C., a loopful of well-grown cells are harvested and fatty acid methyl esters are prepared, separated and identified using the Sherlock Microbial Identification System (MIDI) as described (see Vandamme et al., 1992). The predominant fatty acids present in the Burkholderia A396 are as follows: 16:0 (24.4%), cyclo 17:0 (7.1%), 16:0 3-OH (4.4%), 14:0 (3.6%), 19:0 ω8c (2.6%) cyclo, 18:0 (1.0%). Summed feature 8 (comprising 18:1 ω7c) and summed feature 3 (comprising of 16:1 ω7c and 16:1 ω6c) corresponded to 26.2% and 20.2% of the total peak area, respectively. Summed feature 2 comprising 12:0 ALDE, 16:1 iso I, and 14:0 3-OH) corresponded to 5.8% of the total peak area while summed feature 5 comprising 18:0 ANTE and 18:2 ω6,9c corresponded to 0.4%. Other fatty acids detected in A396 in minor quantities included: 13:1 at 12-13 (0.2%), 14:1 ω5c (0.2%), 15:0 3-OH (0.13%), 17:1 ω7c (0.14%), 17:0 (0.15%), 16:0 iso 3-OH (0.2%), 16:0 2-OH (0.8%), 18:1 ω7c 11-methyl (0.15%), and 18:1 2-OH (0.4%).

A comparison of the fatty acid composition of A396 with those of known microbial strains in the MIDI database suggested that the fatty acids in the novel strain A396 were most similar with those of *Burkholderia cenocepacia*.

Resistance to Antibiotics

Antibiotic susceptibility of *Burkholderia* A396 is tested using antibiotic disks on Muller-Hinton medium as described in PML Microbiological's technical data sheet #535. Results obtained after 72-hour incubation at 25° C. are presented in Table 2 below.

TABLE 2

Susceptibility of MBI-206 to various antibiotics.

| | Concentration (ug) | Susceptible |
|---|---|---|
| Tetracycline | 30 | – |
| Kanamycin | 30 | +++ |
| Erythromycin | 15 | – |
| Streptomycin | 10 | – |
| Penicillin | 10 | – |
| Ampicillin | 10 | – |
| Oxytetracycline | 30 | – |
| Chloramphenicol | 30 | ++ |
| Ciprofloxacin | 5 | ++ |
| Gentamicin | 10 | – |
| Piperacillin | 100 | +++ |
| Cefuroxime | 30 | – |
| Imipenem | 10 | +++ |
| Sulphamethoxazole-Trimethoprim | 23.75/25 | ++ |

+++ very susceptible,
++ susceptible,
– resistant

The results indicate that the antibiotic susceptibility spectrum of *Burkholderia* A396 is quite different from pathogenic *B. cepacia* complex strains. *Burkholderia* A396 is susceptible to kanamycin, chloramphenicol, ciprofloxacin, piperacillin, imipenem, and a combination of sulphamethoxazole and trimethoprim. As a comparison, Zhou et al., 2007 tested the susceptibility of 2,621 different strains in *B. cepacia* complex isolated from cystic fibrosis patients, and found that only 7% and 5% of all strains were susceptible to imipenem or ciprofloxacin, respectively. They also found 85% of all strains to be resistant to chloramphenicol (15% susceptible), and 95% to be resistant (5% susceptible) to the combination of sulphamethoxazole and trimethoprim. Results of Zhou et al., 2007 are similar to those of Pitt et al., 1996 who determined antibiotic resistance among 366 *B. cepacia* isolates and reported that most of them are resistant to ciprofloxacin, cefuroxime, imipene.

Example 2

Inactivation of *Burkholderia* Whole Cell Broth

Based on the results from the heat kill time course study for the inactivation of (*Burkholderia* sp. strain A396) a heating period of 60 minutes at 60° C. was selected for testing the *Burkholderia* sp inactivation in ten 10-liter production batch. The production fermentation culture was grown for 48 hours in ten 10-liter water-jacketed glass production fermenters. After 48 hours, the temperature set point was increased to 60° C. to initiate heating. The water in the fermenter jacket was heated via an internal heating loop in the system to raise the temperature of the fermenter culture up to the set point. A 150 ml sample was aseptically removed in triplicate from each fermenter prior to initiation of heating and at 60 minutes after the temperature of the culture reached 60° C. The total time it took to heat the culture to 60° C. was 59 minutes. The 150 ml samples were placed in 250 ml sterile Nalgene containers and stored at room temperature. The samples were then analyzed for any re-growth by an enrichment method.

Example 3

Isolation of Fractions and Substances from Heat Inactivated *Burkholderia A*396

Methods and Materials

The following procedure is used is set forth in FIG. 1.

The culture broth derived from the 10-L fermentation *Burkholderia* (A396) in Hy soy growth medium is extracted with Amberlite XAD-7 resin (Asolkar et al., 2006) by shaking the cell suspension with resin at 225 rpm for two hours at room temperature after the fermentation is inactivated using the procedure set forth above. The resin and cell mass are collected by filtration through cheesecloth and washed with DI water to remove salts. The resin, cell mass, and cheesecloth are then soaked for 2 h in acetone after which the acetone is filtered and dried under vacuum using rotary evaporator to give the crude extract. The crude extract is then fractionated by using reversed-phase C18 vacuum liquid chromatography ($H_2O/CH_3OH$; gradient 90:10 to 0:100%) to give 11 fractions. These fractions are then concentrated to dryness using rotary evaporator and the resulting dry residues are screened for biological activity using 96 well plate lettuce seeding assay. The active fractions are then subjected to reversed phase HPLC (Spectra System P4000 (Thermo Scientific) to give pure compounds, which are then screened in above mentioned bioassays to locate/identify the active compounds. To confirm the identity of the compound, additional spectroscopic data such as LC/MS and NMR is recorded.

The fraction 4 was purified further by using HPLC C-18 column (Phenomenex, Luna 10u C18(2) 100 A, 250×30), water:acetonitrile gradient solvent system (0-10 min; 80% aqueous $CH_3CN$, 10-25 min; 80-65% aqueous $CH_3CN$, 25-50 min; 65-50% aqueous $CH_3CN$, 50-60 min; 50-70% $CH_3CN$, 60-80 min; 70-0% aqueous $CH_3CN$, 80-85 min;

0-20% aqueous CH$_3$CN) at 8 mL/min flow rate and UV detection of 210 nm, to give templazole B, retention time 46.65 min. The active fraction 5 was purified further by using HPLC C-18 column (Phenomenex, Luna 10u C18(2) 100 A, 250×30), water:acetonitrile gradient solvent system (0-10 min; 80% aqueous CH$_3$CN, 10-25 min; 80-65% aqueous CH$_3$CN, 25-50 min; 65-50% aqueous CH$_3$CN, 50-60 min; 50-70% aqueous CH$_3$CN, 60-80 min; 70-0% aqueous CH$_3$CN, 80-85 min; 0-20% aqueous CH$_3$CN) at 8 mL/min flow rate and UV detection of 210 nm, to give FR90128, retention time 66.65 min. The other fraction 6 was also purified using HPLC C-18 column (Phenomenex, Luna 10u C18 (2) 100 A, 250×30), water:acetonitrile gradient solvent system (0-10 min; 80% aqueous CH$_3$CN, 10-25 min; 80-60% aqueous CH$_3$CN, 25-50 min; 60-40% aqueous CH$_3$CN, 50-60 min; 40% CH$_3$CN, 60-80 min; 40-0% aqueous CH$_3$CN, 80-85 min; 0-20% aqueous CH$_3$CN) at 8 mL/min flow rate and UV detection of 210 nm, to give templazole A, retention time 70.82 min.

Mass spectroscopy analysis of pure compounds is performed on a Thermo Finnigan LCQ Deca XP Plus electrospray (ESI) instrument using both positive and negative ionization modes in a full scan mode (m/z 100-1500 Da) on a LCQ DECA XP$^{Plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5 µm column (Phenomenex). The solvent system consists of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 µL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The active compound templazole A has a molecular mass of 298 and showed m/z ion at 297.34 in negative ionization mode. The LC-MS chromatogram for templazole B suggests a molecular mass of 258 and exhibited m/z ion at 257.74 in negative ionization mode.

$^1$H, $^{13}$C and 2D NMR spectra were measured on a Bruker 500 MHz δ 600 MHz gradient field spectrometer. The reference is set on the internal standard tetramethylsilane (TMS, 0.00 ppm).

Structure Elucidation of Templazole A (i)

The templazole A (1) was obtained as light yellowish solid. The molecular weight of the pure compound was obtained from the HRESITOF mass spectrum which showed a protonated molecular ion at m/z 299.15 [M+H]$^+$, suggesting molecular weight of 298, which is also confirmed by the (−) ESIMS spectrum. The UV absorption bands at 226, 275, 327 nm, suggested the presence of indole and oxazole rings in the molecule. The molecular formula, C$_{17}$H$_{18}$N$_2$O$_3$, was determined by interpretation of $^1$H, $^{13}$C NMR and HRESI MS data m/z 299.1396 (M+H)$^+$ (Calcd for C$_{17}$H$_{19}$N$_2$O$_3$, 299.1397), which entails a high degree of unsaturation shown by 10 double bond equivalents. The $^{13}$C NMR spectrum revealed signals for all 17 carbons, including two methyls, a methoxy, a methylene carbon, an aliphatic methine, an ester carbonyl, and eleven aromatic carbons. The presence of 3'-substituted indole was revealed from $^1$H-$^1$H COSY and HMBC spectral data. The $^1$H-$^1$H COSY and HMBC also indicated the presence of a carboxylic acid methyl ester group and a —CH$_2$—CH—(CH$_3$)$_2$ side chain. From the detailed analysis of $^1$H-$^1$H COSY, $^{13}$C, and HMBC data it was derived that the compound contained an oxazole nucleus. From the 2D analysis it was found that the iso-butyl side chain was attached at C-2 position, a carboxylic acid methyl ester at C-4 position and the indole unit at C-5 position to complete the structure of templazole A (i).

Structure Elucidation of Templazole B(ii)

The compound ii was obtained as a colorless solid, which showed a molecular ion peak at m/z 257.74 in negative ionization mode indicating the molecular weight of 258. The molecular formula, of this compound was assigned as C$_{15}$H$_{18}$N$_2$O$_2$, which was determined by interpretation of $^1$H, $^{13}$C NMR and mass data. The $^{13}$C NMR spectrum revealed signals for all 15 carbons, including two methyls, two methylene carbons, one aliphatic methine, one amide carbonyl, and nine aromatic carbons. The general nature of the structure was deduced from $^1$H and $^{13}$C NMR spectra that showed a para-substituted aromatic ring [δ 7.08 (2H, d, J=8.8 Hz), 6.75 (2H, d, J=8.8 Hz), and 132.7, 129.5, 115.2, 127.3, 115.2, 129.5]. The $^1$H NMR spectrum (FIG. 6) of this structure together with the $^1$H-$^1$H COSY and HSQC spectra, displayed characteristic signals for an isobutyl moiety [δ 0.93 (6H, d, J=6.9 Hz), 2.15 (1H, sept., J=6.9 Hz), 2.57 (2H, d, J=6.9 Hz). In addition, an olefinic/aromatic proton at (δ7.06, s), and a carbonyl carbon group (δ 158.9) were also found in the $^1$H and $^{13}$C NMR spectra. On inspection of the HMBC spectrum, the H-1' signal in the isobutyl moiety correlated with the olefinic carbon (C-2, δ 156.3), and the olefinic proton H-4 correlated with (C-5, δ 155.5; C-2, 156.3 & C-1", 41.2). The methylene signal at δ 3.75 correlated with C-5, C-4 as well as the C-2" of the para-substituted aromatic moiety. All these observed correlation suggested the connectivity among the isobutyl, and the para-substituted benzyl moieties for the skeleton of the structure as shown. In addition, the carboxamide group was assigned at the para position of the benzyl moiety based on the HMBC correlation from the aromatic proton at H-4"& H-6" position. Thus, based on the above data, the structure was designated as templazole B (ii).

Structure Elucidation of FR901228 (iii)

The compound iii was obtained as a colorless solid by bio-assay guided purification of fraction F5. The molecular weight of this compound was derived as 540 based on molecular ion peak at 541 [M+H] and pseudomolecular ion peak at 563 [M+Na] in positive ESIMS. This was well supported by the ionization pattern in the negative ESIMS with the peak at 539 [M−H]. The molecular formula, C$_{24}$H$_{36}$N$_4$O$_6$S$_2$, was determined by the interpretation of NMR analysis and high-resolution ESIMS (obsd. 541.2164; C$_{24}$H$_{36}$N$_4$O$_6$S$_2$+H requires 541.2154). The $^1$H NMR spectrum displayed characteristics of a typical peptide. The $^{13}$C NMR spectrum revealed signals for all 24 carbons, including 5 CH$_3$, 4 CH$_2$, 9 CH and 6 quaternary carbons. Since five amide or ester carbonyls [δ$_c$ 172.9, 172.9, 169.6, 169.2, 167.6, 168.8] and four olefinic carbons [δ$_c$ 130.4 (s), 130.1 (d), 129.9 (d), 128.3 (d)] account for 7 of the 9 degrees of unsaturation required by the molecular formula, compound iii must be a bicyclic compound. A detailed analysis of the $^1$H, and $^1$H-$^1$H-COSY spectrum suggested the presence of two Val residues and an ethylidene group. Research in the Anti-Base with the above information suggested that the compound under investigation was a known molecule designated as FR901228, reported from *Chromobacterium violaceum*

No. 910 (Ueda et al., U.S. Pat. No. 7,396,665). This compound been patented earlier as anticancer compound, however, no pesticidal use has been reported in the literature.

The assigned structure was later confirmed by X-ray crystal data. The crystals were developed in a mixture of acetone and methanol.

Example 4

Characterization of Fractions and Substances from Heat Inactivated *Burkholderia* A396

Glutamine Synthetase Assay

Figure 3:
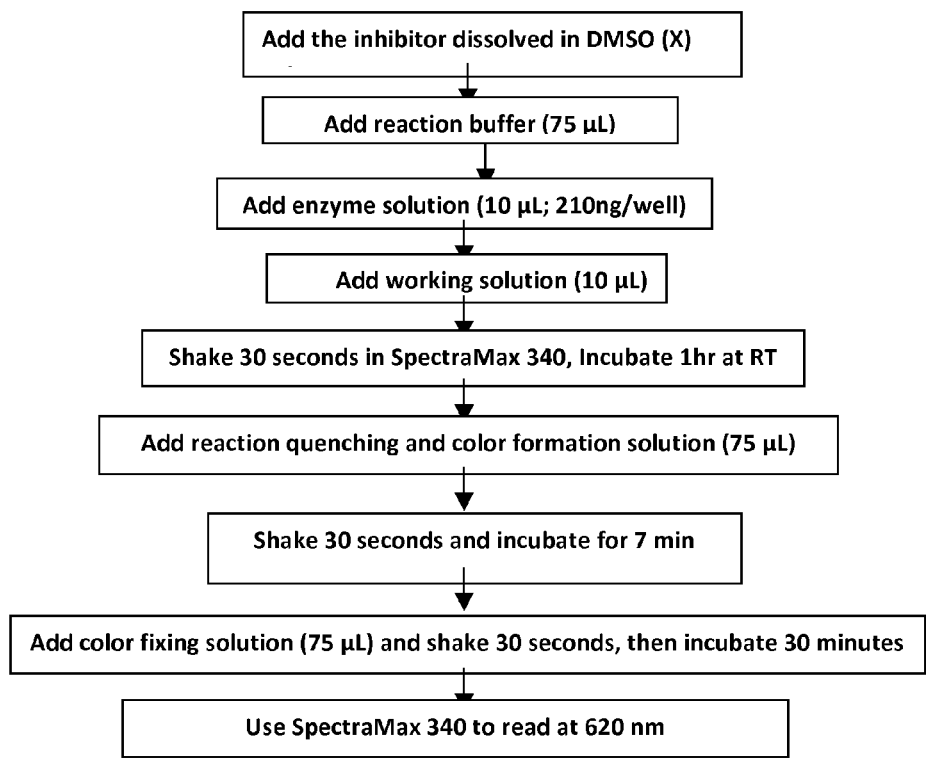
FIG. 3 shows the scheme used to detect plant glutamine synthetase activity in vitro.

The biosynthetic assay for plant glutamine synthetase was carried out as follows. This assay uses following solutions: reaction buffer (pH 6.8, 75 mM HEPES, 300 mM L-glutamic acid, 11 mM $NH_4Cl$, 40 mM $MgCl_2$), recombinant plasmid GS from *Lotus japonicas* (Betti et al., 2006) working solution (pH 6.8, 50 mM ATP), reaction quenching and color formation solution (12% w/v L-ascorbic acid in 1 N HCl solution and 2% w/v sodium molybdate in DD $H_2O$), color fixing solution (1% sodium citrate tribasic dehydrate in 1% acetic acid in DD $H_2O$), and blank solution (420 mM EDTA solution). The assay was performed in a 96-well plate with a total volume of 250 μL as set forth in FIG. 3.

Commercial herbicide (i.e., glufosinate or DL-Phosphinotricin) was used a positive control. EDTA was used as a negative control. In this experiment, we used the active ingredient(s) in the extracts from *Burkholderia* Spp. (internal labeled as A396 strain or MBI-206 and/or MBI-010).

Results

Data (Table 3) suggests that DL-phosphinotricin at a final concentration of 200 μg/ml inhibited about 70% of the activity of the recombinant glutamine synthetase from *Lotus japonicas*, but the crude extract from A396 (i.e., MBI-010) inhibited 63% and 96% of activity at final concentrations of 1 and 10 μg/ml, respectively. However, the fractions from A396 crude extract (F1, F2, F3, F4, F5, F6) did not inhibit the glutamine synthetase activity well. This may have been because of a fermentation media change or a combination interaction of different compounds in crude extracts on the glutamine synthetase.

TABLE 3

Glutamine synthetase inhibition by *Burkholderia*-study #1 (MBI-010)

| Sample | Concentration (μg/ml) | GS inhibition (%) |
| --- | --- | --- |
| Negative | | 0.1 |
| DL-Phosphinotricin | 200 | 70 |
| A396 | 1 | 63 |
| A396 | 10 | 96 |
| A396 (F1) | 1 | 16 |
| A396 (F2) | 1 | 22 |
| A396 (F3) | 1 | 48 |
| A396 (F4) | 1 | 41 |
| A396 (F5) | 1 | 0 |
| A396 (F6) | 1 | 0 |

Results from further studies are shown in Tables 4 and 5. The crude extracts from Pre-HK (pre-heat-killing) and heat-killed whole cell broths did only show less than 40% inhibition. Compared with crude extract (120619ST Crude), some fractions (120619ST F5 and F9) inhibited the GS activity, but some fractions also enhanced the GS activity (120619ST F8 and F10). Compared with the positive control glufosinate (i.e., DL-phosphinotricin) at 100 ppm, both fractions (120619ST F5 and F9) at 40 ppm displayed a lower inhibition. Furthermore, as shown in Table 5, templazole A and B and FR901228 appear to have an inhibitory effect on plant glutamate synthetase activity.

TABLE 4

Glutamine synthetase inhibition by crude extracts of *Burkholderia* and their fractions - Study #2 (MBI-206)

| Sample | Concentration (μg/ml) | GS inhibition (%) Plate 1 | GS inhibition (%) Plate 2 |
| --- | --- | --- | --- |
| Negative | | | 0 |
| DL-Phosphinotricin | 100 | 68.8 | 71.5 |
| 120619ST F1 | 40 | 4 | 2 |
| 120619ST F2 | 40 | 30 | 33 |
| 120619ST F3 | 40 | 26 | 24 |
| 120619ST F4 | 40 | 32 | 26 |
| 120619ST F5 | 40 | 50 | 50 |
| 120619ST F6 | 40 | 24 | 25 |
| 120619ST F7 | 40 | 35 | 39 |
| 120619ST F8 | 40 | −40 | −48 |
| 120619ST F9 | 40 | 59 | 57 |
| 120619ST F10 | 40 | −65 | −65 |
| 120619ST F11 | 40 | 2 | −5 |
| 120619ST Crude | 40 | 39 | 32 |
| 120619ST EA Sep | 40 | 22 | 12 |
| 120808 Pre-HK | 40 | 7 | 23 |

TABLE 5

Glutamine synthetase inhibition by pure compounds of MBI-206 and their fractions

| Sample | Concentration (μg/ml) | GS inhibition (%) |
| --- | --- | --- |
| Negative | | 0 |
| DL-Phosphinotricin | 100 | 70.8 |
| Templazole A (i) | 40 | 30 |
| Templazole B (ii) | 40 | 46 |
| FR901228 (iii) | 40 | 57 |
| 120619ST F5 | 40 | 55 |
| 120619ST F9 | 40 | 51 |

Example 5

Systemic Effect of MBI-010 on Pigweed

Crude extract was applied to pigweed petioles in pots varying doses by adhering an 010- or water-saturated piece of paper towel to a single 0.25 cm stretch of petiole or stem per plant. Two pigweed (*Amaranthus retroflexus*) plants per 4-inch square pot were treated at the 4-5 leaf stage. Pots contained potting soil and were randomly placed in a growth room at 25° C. and 50% RH, and watered as necessary. Treatments were replicated five times and evaluated at 7 and 14 days for visual damage and signs of systemicity, with 0 indicating no damage and 100 indicating plant death; systemic activity was evaluated based on the appearance of symptoms (curling, spotting, chlorosis, necrosis, etc.) on plant areas not directly treated. A slight systemic effect (S−) was defined as observed non-necrotic symptoms such as curling, crinkling or chlorotic spots on 1-2 areas not directly treated; a moderate systemic effect (S) included 3-4 areas of observable symptoms as described above, including 1-2 with necrotic spots; a strong systemic effect (S+) indicated more than 2 necrotic areas or significant (≥33%) whole plant stunting. Application of 100% of crude extract to petioles desiccated the leaf three days after treatment and killed the plant 14 days after treatment.

TABLE 6

Systemic Effects of MBI-10

| Treatment | Replicate 1 | 2 | 3 |
|---|---|---|---|
| Untreated Control on Stem | 0 | 0 | 0 |
| 50% MBI-010 CE on Stem | S | S | S |
| 100% MBI-010 CE on Stem | S+ | S+ | 100 |
| Untreated Control on Petiole | 0 | 0 | 0 |
| 50% MBI-010 CE on Petiole | S− | S− | S− |
| 100% MBI-010 CE on Petiole | S+ | S+ | S+ |

Key:
0: no symptoms,
S−: Systemic, slight effect,
S: Systemic-Moderate effect,
S+: systemic- Strong effect,
100: Plant death Microorganism Deposit The following biological material has been deposited under the terms of the Budapest Treaty with the Agricultural Research Culture Collection (NRRL), 1815 N. University Street, Peoria, Ill. 61604 USA, and given the following number:

| Deposit | Accession Number | Date of Deposit |
|---|---|---|
| Burkholderia sp. A396 | NRRL B-50319 | Sep. 15, 2009 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

CITED REFERENCES

Abdel-Mawgoud, A. M.; Lepine, F.; Deziel, E. (2010). Rhamnolipids: diversity of structures, microbial origins and roles. *Applied Microbiology and Biotechnology* 86: 1323-1336.

Asolkar, R. N. et al., (2006). Weakly cytotoxic polyketides from a marine-derived Actinomycete of the genus *Streptomyces* strain CNQ-085. *J. Nat. Prod.* 69, 1756-1759.

Betti M., Arcondéguy, T. and Marquez A. J. (2006). Molecular analysis of two mutants from *Lotus japonicus* deficient in plastidic glutamine synthetase: functional properties of purified GLN2 enzymes. *Planta* 224: 1068-1079.

Blodget, J. A. V., Zhang, J. K., Metcalf, W. W., (2005). Molecular cloning, sequence analysis and heterologous expression of phosphinothricin tripeptide biosynthetic gene cluster from *streptomyces viridochromogenes* DSM 40736. *Antimicrobial agents and chemotherapy* 49: 230-240.

Burkholder, W. H (1950). Sour skin, a bacterial rot of onion bulbs. *Phytopathology* 40: 115-117.

Caballero-Mellado et al., (2004). *Burkholderia unamae* sp. nov., an N2-fixing rhizospheric and endophytic species. *Int. J. Syst. Evol. Microbiol.* 54: 1165-1172.

Cain, C. C., et al., (2003). Synergistic antimicrobial activity of metabolites produced by a nonobligate bacterial predator. *Antimicrobial Agents and Chemotherapy* 47: 2113-2117.

Casida, et al., U.S. Pat. No. 6,689,357.

Castro-Rodríguez, V., Angel García-Gutiérrez, A. Javier Canales, J. Concepción Avila, C. Kirby, E. and Cánovas, F. (2011). The glutamine synthetase gene family in *Populus, BMC Plant Biology* 11:119.

Chen et al., (2007). *Burkholderia nodosa* sp. nov., isolated from root nodules of the woody Brazilian legumes *Mimosa bimucronata* and *Mimosa scabrella. Int. J. Syst. Evol. Microbiol.* 57: 1055-1059.

Cheng, A. C. and Currie, B. J. (2005). Melioidosis: epidemiology, pathophysiology, and management. *Clin. Microbiol.* 18: 383-416.

Coenye, T. and P. Vandamme, P. (2003). Diversity and significance of *Burkholderia* species occupying diverse ecological niches. *Environ. Microbiol.* 5: 719-729.

Compant, et al. (2008). Diversity and occurence of *Burkholderia* spp. in the natural environment. *FEMS Microbiol. Rev.* 32: 607-626.

Deng, Y.; Wu, J.; Eberl, L. (2010). Structural and Functional Characterization of Diffusible Signal Factor Family Quorum-Sensing Signals Produced by Members of the *Burkholderia cepacia* Complex. *Applied and environmental microbiology* 76: 4675-4683.

El-Banna, N.; Winkelmann, G. (1998). Pyrrolnitrin from *Burkholderia cepacia*: antibiotic activity against fungi and novel activities against *Streptomycetes. J. Applied Microbiology* 85: 69-78.

Eisenberg (2000). Structure-function relationships of glutamine synthetases. *BBA* 1477:122-135, Gawronski, J. D., Benson, D. R. (2004). Microtiter assay for glutamine synthetase biosynthetic activity using inorganic phosphate detection. *Analytical Biochemistry* 327: 114-118.

Gising, J., Nilsson, M. T., Odell, L. R., Yahiaoui, S., Lindh, M., Iyer, H., Sinha, A. M., Srinivasa, B. R., Larhed, M., Mowbray, S. L., Karle'n, A. (2012). Trisubstituted Imidazoles as *Mycobacterium tuberculosis* Glutamine Synthetase Inhibitors, *J. Medicinal Chemistry* 55: 2894-2898.

Gouge et al., US Patent Application Pub. No. 2003/0082147.

Harth, G., Horwitz, M. A. (1999). An inhibitor of exported *Mycobacterium tuberculosis* glutamine synthetase selectively blocks the growth of pathgogenic mycobacteria in Axenic culture and in human monocytes: extracellular proteins as potential novel drug targets *J. Exp. Med.,* 189: 1425-1435.

Harth, G.; Zamecnik, P. C.; Tang, J. Y.; Tabatadze, D.; Horwitz, M. A. (2000). Treatment of *Mycobacterium tuberculosis* with antisense oligonucleotides to glutamine synthetase mRNA inhibits glutamine synthetase activity, formation of the poly-L-glutamate/glutamine cell wall structure, and bacterial replication, *Proc Natl Acad Sci USA* 97:418-423.

Henderso, P. J.; Lardy, H. A. (1970). Bongkerekic acid—An inhibitor of adenine nucleotide translocase of mitochondria. *J. Biological Chemistry* 245: 1319-26.

Holmes, A.; Govan, J.; Goldstein, R. (1998). Agricultural use of *Burkholderia* (*Pseudomonas*) *cepacia*: A threat to human health? *Emerging Infectious Diseases* 4: 221-227.

Jansiewicz, W. J. and Roitman J. (1988). Biological control of blue mold and gray mold on apple and pear with *Pseudomonas cepacia*. *Phytopathology* 78: 1697-1700.

Jeddeloh et al., WO2001/055398.

Jeong, Y., et al., (2003). Toxoflavin produced by *Burkholderia glumae* causing rice grain rot is responsible for inducing bacterial wilt in many field crops. *Plant Disease*, 87, 890-895.

Keum, Y. S., et al., (2009). Effects of Nutrients on Quorum Signals and Secondary Metabolite Productions of *Burkholderia* sp O33. *J. Microbiology and Biotechnology*, 19, 1142-1149.

Knudsen, G. R. and Spurr, J. (1987). Field persistence and efficacy of five bacterial preparations for control of peanut leaf spot. *Plant Disease* 71: 442-445.

Koga-Ban, Y., et al., (1995). cDNA sequences of three kinds of beta-tubulins from rice. *DNA Research*, 2, 21-26.

LaRossa, R. A., and Schloss, J. V. (1984). The sulfonylurea herbicide sulfometuron methyl is an extremely potent and selective inhibitor of acetolactate synthase in *Salmonella typhimurium*, *Journal of Biological Chemistry*, 259: 8753-8757.

Lea, P. J., Joy, K. W., Ramos, J. L., Guerrero, M. G. (1984). The action of 2-amino-4-(methylphosphinyl)-butanoic acid (Phosphinothricin) and its 2-oxo-derivative on the metabolism of cyanobacteria and higher plants. *Phytochemistry* 23: 1-6.

Leahy et al., (1996). Comparison of factors influencing trichloroethylene degradation by toluene-oxidizing bacteria. *Appl. Environ. Microbiol.* 62: 825-833.

Lee, C. H., et al., (1994). Cepacidine-A, a novel antifungal antibiotic produced by *Pseudomonas-cepacia*. 1. Taxonomy, production, isolation and biological activity. *J. Antibiotics* 47: 1402-1405.

Lorch, H et al., (1995). Basic methods for counting microoganisms in soil and water. In *Methods in applied soil microbiology and biochemistry*. K. Alef and P. Nannipieri. Eds. San Diego, Calif., Academic Press: pp. 146-161. 1995.

Ludovic et al. (2007). *Burkholderia* diveristy and versatility: An inventory of the extracellular products. *J. Microbiol. Biotechnol.* 17: 1407-1429.

Mao, S., et al., (2006). Isolation and characterization of antifungal substances from *Burkholderia* sp culture broth. *Current Microbiology*, 53: 358-364.

Meyers, E., et al., (1987). Xylocandin A new complex of antifungal peptides. 1. Taxonomy, isolation and biological activity. *J. Antibiotics*, 40: 1515-1519.

Moon, S. S., et al., (1996). Plant growth promoting and fungicidal 4-quinolinones from *Pseudomonas cepacia*. *Phytochemistry*, 42: 365-368.

Morita, Y., et al., (2003). Biological activity of tropolone. *Biological & Pharmaceutical Bulletin*, 26: 1487-1490.

Nagamatsu, T. (2001) "Syntheses, transformation, and biological activities of 7-azapteridine antibiotics: toxoflavin, fervenulin, reumycin, and their analogs". *Recent Res. Devel. Org. Bioorg. Chem.* 4: 97-121.

Nierman et al., (2004). Structural flexibility in the *Burkholderia mallei* genome. *Proc. Natl. Acad. Sci. USA* 101: 14246-14251.

Parke, et al. U.S. Pat. No. 6,077,505.

Partida-Martinez, L. P.; C. Hertweck, A. (2007). Gene cluster encoding rhizoxin biosynthesis in *Burkholderia rhizoxina*, the bacterial endosymbiont of the fungus *Rhizopus microsporus*. *Chembiochem*, 8: 41-45.

Okazaki, S.; Sugawara, M.; Minamisawa, K. (2004). *Bradyrhizobium elkanii* rtxC gene is required for expression of symbiotic phenotypes in the final step of rhizobitoxine biosynthesis. *Applied and Environmental Microbiology*, 70, 535-541.

Selvakumar, D., Dey, S., Das, D. (1999). Production and bioassay of bialaphos biosynthesized by *Streptomyces hydroscopicus* NRRL B-16256, *Bioprocess Engineering* 20:459-462.

Shoji, J., et al., (1990). Isolation of Cepafungin-I, Cepafungin-II and Cepafungin-III from *Pseudomonas* species. *J. Antibiotics*, 43, 783-787.

Singh, U., Panchanadikar, V., Sarkar, D. (2005). Development of a simple assay protocol for high-throughput screening of *Mycobacterium tuberculosis* Glutamine Synthetase for the Identification of Novel Inhibitors, *Journal of Biomolecular Screening*, 10(7): 725-729.

Singh, U., Sarkar, D. (2006). Development of a simple high-throughput screening protocol based on biosynthetic activity of *Mycobacterium tuberculosis* glutamine synthetase for the identification of novel inhibitors, *J Biomol Screen* 11: 1035-1042.

Stead, P., et al., (2008). Induction of phenazine biosynthesis in cultures of *Pseudomonas aeruginosa* by L-N-(3-oxohexanoyl) homoserine lactone. Fems Microbiology Letters 140: 15-22.

Sultan, M. Z., et al., (2008). Novel oxidized derivatives of antifungal pyrroInitrin from the bacterium *Burkholderia cepacia* K87. J. Antibiotics 61: 420-425.

Tachibana, K., Watanabe, T., Sekizawa, Y., Takematsu, T., (1986). Inhibition of glutamine synthetase and quantitative changes of free amino acids in shoots of bialaphos treated Japanese Barnyard millet, J. Pesticide Science, 11:27-31.

Tsuruo, T., et al., (1986). Rhizoxin, macrocyclic lactone antibiotics, as a new antitumor agent against human and murine rumor-cells and their vincristine-resistant sublines. *Cancer Research*, 46, 381-385.

Ueda et al., U.S. Pat. No. 7,396,665.

US Patent Appln. Pub. No. 20100022584

Vanderwall et al., (1997). A model of the structure of HOO-Co.bleomycin bound to d(CCAGTACTGG): recognition at the d(GpT)site and implications for double-stranded DNA cleavage, *Chem. Biol.* 4, 373-387.

Vencill, W. K., Nichols, R. L., Webster, T. M., Soteres, J. K., Mallory-Smith, C., Burgos, N. R., Johnson, W. G., McClelland, M. R. (2012). Herbicide resistance: toward an understanding of resistance development and the impact of herbicide-resistant crops, 2012, *Weed Science Special Issue:* 2-30.

Zhang et al., U.S. Pat. No. 7,141,407.

What is claimed is:

1. A method for identifying a substance that modulates plant glutamine synthetase activity in vitro comprising the steps of:

(a) contacting a plant glutamine synthetase with a test plant glutamine synthetase modulator that comprises an isolated culture or a whole cell broth of *Burkholderia* A396 (NRRL Accession No. B-50319);

(b) determining whether or not the activity of the glutamine synthetase is modulated relative to the activity of a plant glutamine synthetase that has not been contacted with the test plant glutamine synthetase modulator;

(c) comparing the activity of the plant glutamine synthetase when contacted with the test plant glutamine synthetase modulator with the activity of the plant glutamine synthetase when contacted with a known plant glutamine synthetase modulator;

(d) applying said test plant glutamine synthetase modulator to at least a portion of a plant; and (e) determining if said test plant glutamine synthetase modulator has herbicidal activity.

2. The method of claim 1, wherein said microorganism comprises a 16S rRNA gene sequence comprising the forward sequence having at least 99% identity to the sequence set forth in SEQ ID NO: 8, 11, 12 and a reverse sequence having at least 99% identity to the sequence set forth in SEQ ID NO: 9, 10, 13, 14 and 15.

3. A method for identifying an herbicidal substance comprising the steps of:

(a) identifying a substance that inhibits plant glutamine synthetase activity by;

(i) contacting a plant glutamine synthetase with a glutamine synthetase modulator that comprises an isolated culture or a whole cell broth of *Burkholderia* A396 (NRRL Accession No. B-50319);

(ii) determining a modulated activity for the plant glutamine synthetase contacted with the glutamine synthetase modulator;

(iii) comparing the modulated activity to a native activity of a plant glutamine synthetase that has not been contacted with the glutamine synthetase modulator;

(b) applying said substance to a plant or plant part; and (c) determining if said substance identified as a glutamine synthetase inhibitor in (a) has herbicidal activity.

4. The method of claim 3, wherein said microorganism comprises a 16S rRNA gene sequence comprising the forward sequence having at least 99% identity to the sequence set forth in SEQ ID NO: 8, 11, 12 and a reverse sequence having at least 99% identity to the sequence set forth in SEQ ID NO: 9, 10, 13, 14 and 15.

* * * * *

SEQUENCE LISTING

<160> NUMBER OF SEQ ID NOS: 15

<210> SEQ ID NO 1

```
<211> LENGTH: 20
<212> TYPE: DNA
<213> ORGANISM: Artificial Sequence
<220> FEATURE:
<223> OTHER INFORMATION: forward primer 27F

<400> SEQUENCE: 1
agagtttgat cctggctcag                                               20

<210> SEQ ID NO 2
<211> LENGTH: 20
<212> TYPE: DNA
<213> ORGANISM: Artificial Sequence
<220> FEATURE:
<223> OTHER INFORMATION: reverse primer, 907R

<400> SEQUENCE: 2
ccgtcaattc ctttgagttt                                               20

<210> SEQ ID NO 3
<211> LENGTH: 16
<212> TYPE: DNA
<213> ORGANISM: Artificial Sequence
<220> FEATURE:
<223> OTHER INFORMATION: 530F

<400> SEQUENCE: 3
gtgccagccg ccgcgg                                                   16

<210> SEQ ID NO 4
<211> LENGTH: 16
<212> TYPE: DNA
<213> ORGANISM: Artificial Sequence
<220> FEATURE:
<223> OTHER INFORMATION: 1114F

<400> SEQUENCE: 4
gcaacgagcg caaccc                                                   16

<210> SEQ ID NO 5
<211> LENGTH: 17
<212> TYPE: DNA
<213> ORGANISM: Artificial Sequence
<220> FEATURE:
<223> OTHER INFORMATION: 1525R

<400> SEQUENCE: 5
aaggaggtgw tccarcc                                                  17

<210> SEQ ID NO 6
<211> LENGTH: 15
<212> TYPE: DNA
<213> ORGANISM: Artificial Sequence
<220> FEATURE:
<223> OTHER INFORMATION: 1100R

<400> SEQUENCE: 6
gggttgcgct cgttg                                                    15

<210> SEQ ID NO 7
<211> LENGTH: 18
<212> TYPE: DNA
<213> ORGANISM: Artificial Sequence
<220> FEATURE:
<223> OTHER INFORMATION: 519R

<400> SEQUENCE: 7
```
gwattaccgc ggckgctg                                                    18

<210> SEQ ID NO 8
<211> LENGTH: 871
<212> TYPE: DNA
<213> ORGANISM: Artificial Sequence
<220> FEATURE:
<223> OTHER INFORMATION: Forward sequence, DNA sequence with 27F primer,
      815 nucleotides

<400> SEQUENCE: 8
tgcagtcgaa cggcagcacg ggtgcttgca cctggtggcg agtggcgaac gggtgagtaa    60
tacatcggaa catgtcctgt agtgggggat agcccggcga aagccggatt aataccgcat   120
acgatctacg gatgaaagcg ggggatcttc ggacctcgcg ctatagggtt ggccgatggc   180
tgattagcta gttggtgggg taaaggccta ccaaggcgac gatcagtagc tggtctgaga   240
ggacgatcag ccacactggg actgagacac ggcccagact cctacgggag gcagcagtgg   300
ggaattttgg acaatggggg aaaccctgat ccagcaatgc cgcgtgtgtg aagaaggcct   360
tcgggttgta aagcactttt gtccggaaag aaatcctttg gctaatacc ccgggggat    420 gacggtaccg gaagaataag caccggctaa ctacgtgcca gcagccgcgg taatacgtag   480
ggtgcgagcg ttaatcggaa ttactgggcg taaagcgtgc gcaggcggtt tgttaagaca   540
gatgtgaaat ccccgggctt aacctgggaa ctgcatttgt gactggcaag ctagagtatg   600 gcagagggg gtagaattcc acgtgtagca gtgaaatgcg tagagatgtg gaggaatacc   660
gatggcgaag gcagcccct gggccaatac tgacgctcat gcacgaaagc gtggggagca   720
aacaggatta gataccctgg tagtccacgc cctaaacgat gtcaactagt tgttggggat   780
tcatttcctt agtaacgtag ctacgcgtga agttgaccgc ctgggagta cggtcgcaag   840 attaaatmga gggtkgkktg kkgggggaa a                                   871

<210> SEQ ID NO 9
<211> LENGTH: 1453
<212> TYPE: DNA
<213> ORGANISM: Artificial Sequence
<220> FEATURE:
<223> OTHER INFORMATION: Reverse sequence, 1453 bp, using primers 1525R,
      1100R, 519R

<400> SEQUENCE: 9
gtcatgaatc ctaccgtggt gaccgtcctc cttgcggtta gactagccac ttctggtaaa    60
acccactccc atggtgtgac gggcggtgtg tacaagaccc gggaacgtat tcaccgcggc   120
atgctgatcc gcgattacta gcgattccag cttcatgcac tcgagttgca gagtgcaatc   180
cggactacga tcggttttct gggattagct cccctcgcg ggttggcaac cctctgttcc    240
gaccattgta tgacgtgtga agccctaccc ataagggcca tgaggacttg acgtcatccc   300
caccttcctc cggtttgtca ccggcagtct ccttagagtg ctcttgcgta gcaactaagg   360
acaagggttg cgctcgttgc gggacttaac ccaacatctc acgacacgag ctgacgacag   420
ccatgcagca cctgtgtatc ggttctcttt cgagcactcc cgaatctctt caggattccg   480
accatgtcaa gggtaggtaa ggttttcgc gttgcatcga attaatccac atcatccacc   540
gcttgtgcgg gtccccgtca attcctttga gttttaatct tgcgaccgta ctccccaggc   600
ggtcaacttc acgcgttagc tacgttacta aggaaatgaa tccccaacaa ctagttgaca   660
tcgtttaggg cgtggactac cagggtatct aatcctgttt gctccccacg ctttcgtgca   720

```
tgagcgtcag tattggccca gggggctgcc ttcgccatcg gtattcctcc acatctctac      780
gcatttcact gctacacgtg gaattctacc ccctctgcc atactctagc ttgccagtca       840
caaatgcagt tcccaggtta agcccgggga tttcacatct gtcttaacaa accgcctgcg     900
cacgctttac gcccagtaat tccgattaac gctcgcaccc tacgtattac cgcggctgct     960
ggcacgtagt tagccggtgc ttattcttcc ggtaccgtca tccccccggg gtattagccc    1020
aaaggatttc tttccggaca aaagtgcttt acaacccgaa ggccttcttc acacacgcgg   1080
cattgctgga tcagggtttc ccccattgtc caaaattccc cactgctgcc tcccgtagga  1140
gtctgggccg tgtctcagtc ccagtgtggc tgatcgtcct ctcagaccag ctactgatcg   1200
tcgccttggt aggcctttac cccaccaact agctaatcag ccatcggcca accctatagc   1260
gcgaggtccg aagatccccc gctttcatcc gtagatcgta tgcggtatta atccggcttt    1320
cgccgggcta tccccacta caggacatgt tccgatgtat tactcacccg ttcgccactc    1380
gccaccaggt gcaagcaccc gtgctgccgt tcgacttgca tgtgtaaggc atgccgccag 1440
cgttcaatct gag                                                                            1453
```

<210> SEQ ID NO 10
<211> LENGTH: 860
<212> TYPE: DNA
<213> ORGANISM: Artificial Sequence
<220> FEATURE:
<223> OTHER INFORMATION: Reverse sequence 824 bp using primer 907R

<400> SEQUENCE: 10

```
ccaggcggtc acttcacgcg ttagctacgt tactaaggaa atgaatcccc aacaactagt       60
tgacatcgtt tagggcgtgg actaccaggg tatctaatcc tgtttgctcc ccacgctttc      120
gtgcatgagc gtcagtattg gcccaggggg ctgccttcgc catcggtatt cctccacatc     180
tctacgcatt tcactgctac acgtggaatt ctaccccccct ctgccatact ctagcttgcc    240
agtcacaaat gcagttccca ggttaagccc ggggatttca catctgtctt aacaaaccgc   300
ctgcgcacgc tttacgccca gtaattccga ttaacgctcg caccctacgt attaccgcgg    360
ctgctggcac gtagttagcc ggtgcttatt cttccggtac cgtcatcccc cggggtatt      420 agcccaaagg atttctttcc ggacaaaagt gctttacaac ccgaaggcct tcttcacaca   480
cgcggcattg ctggatcagg gtttcccca ttgtccaaaa ttccccactg ctgcctcccg       540
taggagtctg ggccgtgtct cagtcccagt gtggctgatc gtcctctcag accagctact     600
gatcgtcgcc ttggtaggcc tttaccccac caactagcta atcagccatc ggccaaccct    660
atagcgcgag gtccgaagat cccccgcttt catccgtaga tcgtatgcgg tattaatccg   720
gctttcgccg gctatcccc cactacagga catgttccga tgtattactc acccgttcgc    780
cactcgccac caggtgcaag cacccgtgct gccgttcgac ttgcatgtgt aaggcatgcc  840
gccagcgttc aatctgagtg                                                                   860
```

<210> SEQ ID NO 11
<211> LENGTH: 1152
<212> TYPE: DNA
<213> ORGANISM: Artificial Sequence
<220> FEATURE:
<223> OTHER INFORMATION: Forward sequence 1152 bp using primer 530F

<400> SEQUENCE: 11

```
tcggattact gggcgtaagc gtgcgcaggc ggtttgttaa gacagatgtg aaatccccgg       60
gcttaacctg ggaactgcat ttgtgactgg caagctagag tatggcagag gggggtagaa   120
```

```
ttccacgtgt agcagtgaaa tgcgtagaga tgtggaggaa taccgatggc gaagggagcc      180
ccctgggcct atactgaccc tcatgctcga aagcgtgagg acccaaccgg attagatgcc      240
ctgataggcc atgccccaca ccatgccatg tgttagggc  ccatttcctt agggaggcag      300 ctatgggaa  ttttgacaa  tgtgggaaac cctgatccaa caatgccgcg tgtgtgaata      360
aggccttcgg gttgtaaagc acttttatcc ggatagattc cttttgggct aaacctccgt      420 agggatgac  ggtaccggaa gaataaccac cgggtaacta cgtgccagca gccgcggtaa      480
tacgtagggt gcgagcgtta atcggaatta ctgggcgtaa agcgtgcgca ggcggtttgt      540
taagacagat gtgaaatccc cgggcttaac ctgggaactg catttgtgac tggcaagcta      600
gagtatggca gacggggta  gaattccacg tgtagcagtg aaatgcgtag agatgtggag      660
gaataccgat gggcgaagca gctcctgggg caatactgac gctcatgcac aagatcgtgc      720
gaaacaaaca ggataaaacc cctgtattcc acgcccaaaa cgatgtccac caagttgttg      780
gcgatccttt ccttcgtatc gtagctacgc gggaatttga ccccctgggg actaggccgc      840
atataaaact caagggaatt ccggggaccc ccagagctgt gtatgatgtg attattccga      900 tgcgcgaaa  accttcctta tctttgaatg gcggtactcc tgaaaattgc ggagtgctcg      960
aaaacaccga acccgggtct ttctgcgtgt cctccctcgt gtgggatatg ctggatatcc     1020
cgcagacgca tctttgactt agtgctccca aaactgagag ctgggaggac tcgagagggg     1080
atccctgcct ccccggcttg ggtgctcccc ttatggggga aacaggtaca cgggggatc     1140 atcccatacc ta                                                         1152

<210> SEQ ID NO 12
<211> LENGTH: 1067
<212> TYPE: DNA
<213> ORGANISM: Artificial Sequence
<220> FEATURE:
<223> OTHER INFORMATION: Forward sequence 1067 bp using 1114F primer

<400> SEQUENCE: 12
tctaaggaga ctgccggtga caaaccggag gaaggtgggg atgacgtcaa gtcctcatgg       60
cccttatggg tagggcttca cacgtcatac aatggtcgga acagagggtt gccaacccgc      120 gaggggagc  taatcccaga aaaccgatcg tagtccggat tgcactctgc aactcgagtg      180
catgaagctg gaatcgctag taatcgcgga tcagcatgcc gcggtgaata cgttcccggg      240
tcttgtacac accgcccgtc acaccatggg agtgggtttt accagaagtg gctagtctaa      300
ccgcaaggag gacggtcacc acggtaggat tcatgactgg ggtgaagtcg taacaaggta      360
gccgtatcgg aaggtgcggc tggatcacct ccttaaaccc tttggcctaa taccccggg       420 ggataagta  ccgaaaaaaa aaaaaactgg ataacttccg tgccacaacc cgcggaaaaa      480
tctagggggg gggagcttaa atggaaattt acggggccgt aaagcgtgcg caggcggttt      540
gtaaacacag atgtgaaatc cccgggctta acctgggaac tgcatttgtg actggcaagc      600
tagagtatgg cacaggggg  tagaattcca cgtgtagcat tgaatgcata gagatgagag      660
gataccgatg gagaagggcg ccccgggga  caatatgacg cctatgccac aaagctgtgg      720
cacaataggt taaatacctg tgttgtcccc gcctaaacag attacacttg ttgtgggtat      780
tttctcataa aatactacac acgggagaat acactggggg gcttcgtcaa ttatcacaac      840
aatgattgcg ggcaccacg  ggggtagatg ggtaataaat cgacggcaac tatctactta      900 cttgatgat  cgcacagatt gggcgggaga gaagagaaca gcgtgtgtgt gctcctccgc      960
```

```
gagtgatagg taatcggaca atactttgac aggacttaac tgggtagcgg gatcgagtgg    1020
attcccgtcg gatggcctcc gcaggtacgg cagctgggga ttacatc                  1067

<210> SEQ ID NO 13
<211> LENGTH: 1223
<212> TYPE: DNA
<213> ORGANISM: Artificial Sequence
<220> FEATURE:
<223> OTHER INFORMATION: Reverse sequence 1223 bp using 1525R primer

<400> SEQUENCE: 13
ttgcttacga cttcacccca gtcatgaatc ctaccgtggt gaccgtcctc cttgcggtta      60
gactagccac ttctggtaaa acccactccc atggtgtgac gggcggtgtg tacaagaccc     120
gggaacgtat tcaccgcggc atgctgatcc gcgattacta gcgattccag cttcatgcac     180
tcgagttgca gagtgcaatc cggactacga tcggttttct gggattagct ccccctcgcg     240
ggttggcaac cctctgttcc gaccattgta tgacgtgtga agccctaccc ataagggcca     300
tgaggacttg acgtcatccc caccttcctc cggtttgtca ccggcagtct ccttagagtg     360
ctcttgcgta gcaactaagg acaagggttg cgctcgttgc gggacttaac ccaacatctc     420
acgacacgag ctgacgacag ccatgcagca cctgtgtatc ggttctcttt cgagcactcc     480
cgaatctctt caggattccg accatgtcaa gggtaggtaa ggttttcgc gttgcatcga     540 attaatccac atcatccacc gcttgtgcgg gtccccgtca attcctttga gttttaatct     600
tgcgaccgta ctccccaggc ggtcaacttc acgcgttagc tacgttacta aggaaatgaa     660
tccccaacaa ctagttgaca tcgtttaggg cgtggactac cagggtatct aatcctgttt     720
gctccccacg ctttcgtgca tgagcgtcag tattggccca ggggctgcc ttcgccatcg      780 gtattcctcc acatctctac gcatttcact gctacacgtg gaattctacc ccctctgcc     840 atactctagc ttgccagtca caaatgcagt tcccaggtta agcccgggga tttcacatct     900
gtcttaacaa accgcctgcg cacgctttac gcccagtaat tccgattaac gctcgcaccc     960
tacgtattac cgcggctgct ggcacgtagt tagccggtgc ttattctgcg gtaccgtcat    1020
cccccgggta tagcccaaag gattctttcg acaaagtgct ttacacccga tgtctctcac    1080
acacgcgcat gctgatcagg tttccccatg tcaaagtcca ctgctgctcg taggtctgga   1140
cgggttcagt tcaatgtgac tgatcgtctt tcgacaacta ctgaacgtcc ctgtagctta    1200
cccaccaact agctatagca tgc                                            1223

<210> SEQ ID NO 14
<211> LENGTH: 1216
<212> TYPE: DNA
<213> ORGANISM: Artificial Sequence
<220> FEATURE:
<223> OTHER INFORMATION: Reverse sequence 1216 bp using 1100R primer

<400> SEQUENCE: 14
ccgagctgac gacagccatg cagcacctgt gtatcggttc tctttcgagc actcccgaat      60
ctcttcagga ttccgaccat gtcaagggta ggtaaggttt tcgcgttgc atcgaattaa     120 tccacatcat ccaccgcttg tgcgggtccc cgtcaattcc tttgagtttt aatcttgcga     180
ccgtactccc caggcggtca acttcacgcg ttagctacgt tactaaggaa atgaatcccc     240
aacaactagt tgacatcgtt tagggcgtgg actaccaggg tatctaatcc tgtttgctcc     300
ccacgctttc gtgcatgagc gtcagtattg gcccaggggg ctgccttcgc catcggtatt     360
cctccacatc tctacgcatt tcactgctac acgtggaatt ctacccccct ctgccatact     420
```

```
ctagcttgcc agtcacaaat gcagttccca ggttaagccc ggggatttca catctgtctt    480
aacaaaccgc ctgcgcacgc tttacgccca gtaattccga ttaacgctcg caccctacgt    540
attaccgcgg ctgctggcac gtagttagcc ggtgcttatt cttccggtac cgtcatcccc    600
ccggggtatt agcccaaagg atttctttcc ggacaaaagt gctttacaac ccgaaggcct    660
tcttcacaca cgcggcattg ctggatcagg gtttccccca ttgtccaaaa ttccccactg    720
ctgcctcccg taggagtctg ggccgtgtct cagtcccagt gtggctgatc gtcctctcag    780
accagctact gatcgtcgcc ttggtaggcc tttaccccac caactagcta atcagccatc    840
ggccaaccct atagcgcgag gtccgaagat cccccgcttt catccgtaga tcgtatgcgg    900
tattaatccg gctttcgccg ggctatcccc cactacagga catgttccga tgtattactc    960
acccgttcgc cactcgcccc aggtgcaagc acccgtgctg ccgttcgact tgcatgtgta   1020
gcatgcgcag cgtcatctac taaataaaca actctaagaa ttttgcccg agggcctcta   1080 aacactcggg gcgtcgagag agactacgga tgaggagcat ccctctgtct ctaggtatgt   1140
gttgtcgcct ctctcacaga ggaggggacg cacgacggag ccatcgggga cgacaacatg   1200
tacgatatac tatcta                                                   1216
```

<210> SEQ ID NO 15
<211> LENGTH: 1194
<212> TYPE: DNA
<213> ORGANISM: Artificial Sequence
<220> FEATURE:
<223> OTHER INFORMATION: Reverse sequence 1194 bp using 519R primer

<400> SEQUENCE: 15

```
ttcttcggta ccgtcatccc cccggggtat tagcccaaag gatttctttc cggacaaaag     60
tgctttacaa cccgaaggcc ttcttcacac acgcggcatt gctggatcag ggtttccccc    120
attgtccaaa attccccact gctgcctccc gtaggagtct gggccgtgtc tcagtcccag    180
tgtggctgat cgtcctctca gaccagctac tgatcgtcgc cttggtaggc ctttacccca    240
ccaactagct aatcagccat cggccaaccc tatagcgcga ggtccgaaga tcccccgctt    300
tcatccgtag atcgtatgcg gtattaatcc ggctttcgcc gggctatccc ccactacagg    360
acatgttccg atgtattact cacccgttcg ccactcgcca ccaggtgcaa gcacccgtgc    420
tgccgttcga cttgcatgtg taaggcatgc cgccagcgtt caatctgagc catgatcaaa    480
ctctgagggg gggggccttc aacggaacga ctgggcaaaa agcgtgccca ggcgttttgt    540
taagacagat gtgaaacccc ggggcttaac ctggaaactg catttgtgac tggaaagcta    600
gagtatggca gaggggggta gaattccacg tgtagcattg aaatgcgtag aaatggagag    660
gaataccgat gggagagggc agcccccgtg ggcaaatact ggcgcttatg aacaaagttg    720
gggcgcgccg ccgggatatg ttcccctggg atatccccccc cctaaactgc ttacaaatat    780
tgtgtgggaa acttttctc taaaaaatag aacacaacgg gagatatcac ccccgggggg    840
ccaccgccag attaaacccc caaaagtat ttggcgggca cccccccggg gggtgagatg    900
gggtaaaata aatccgtgcg acgagcaaac cctccccaca cctgggatgg tcgcgaccac    960
agatgagatg cgggcggaga gaacgatacc caagcgtggt tgtttgcctg catcccctcc   1020
gtcgggagtg gatatagtag agtaattacg gcacgactgc attttttttt cttcagtaca   1080
ccttatcaca ctgttggatg caccgcgaga aatccggagg tgtgagtact ccccccctct   1140
cctcgggatg tgtcggcgct cccttctccc gttcaggggt gggtaagcac cgcg          1194
```